(12) United States Patent
Lee et al.

(10) Patent No.: US 8,744,231 B2
(45) Date of Patent: Jun. 3, 2014

(54) METHOD OF DISPLAYING IMAGE TAKEN BY CAPSULE ENDOSCOPE AND RECORD MEDIA OF STORING PROGRAM FOR CARRYING OUT THAT METHOD

(75) Inventors: Dong Ha Lee, Anyang-si (KR); Tae Gwon Kim, Seongnam-si (KR)

(73) Assignee: Intromedic, Seoul (KR)

( * ) Notice: Subject to any disclaimer, the term of this patent is extended or adjusted under 35 U.S.C. 154(b) by 870 days.

(21) Appl. No.: 12/572,537

(22) Filed: Oct. 2, 2009

(65) Prior Publication Data

US 2010/0086286 A1     Apr. 8, 2010

(30) Foreign Application Priority Data

Oct. 7, 2008  (KR) .......................... 10-2008-0098111
Nov. 14, 2008  (KR) .......................... 10-2008-0113153

(51) Int. Cl.
*H04N 5/77* (2006.01)
*H04N 9/80* (2006.01)
*G06F 3/00* (2006.01)
*A61B 1/00* (2006.01)
*A61B 1/04* (2006.01)

(52) U.S. Cl.
USPC ........... 386/224; 386/239; 715/700; 715/719; 600/101; 600/109

(58) Field of Classification Search
CPC ................ H04N 2005/2255; H04N 2005/225; G06F 19/3406; G06F 19/36; A61B 1/00; A61B 5/00; A61B 5/0033; A61B 5/0037; A61B 5/004; A61B 1/041
See application file for complete search history.

(56) References Cited

U.S. PATENT DOCUMENTS

| | | | |
|---|---|---|---|
| 7,119,814 B2 | 10/2006 | Meron et al. | |
| 7,505,062 B2 | 3/2009 | Davidson et al. | |
| 2002/0012134 A1* | 1/2002 | Calaway | 358/1.18 |
| 2004/0212586 A1* | 10/2004 | Denny, III | 345/156 |
| 2004/0249291 A1* | 12/2004 | Honda et al. | 600/476 |
| 2005/0114179 A1* | 5/2005 | Brackett et al. | 705/2 |
| 2008/0184168 A1* | 7/2008 | Oda | 715/838 |
| 2008/0232702 A1* | 9/2008 | Kimoto | 382/232 |
| 2009/0089056 A1* | 4/2009 | Fujii | 704/246 |

FOREIGN PATENT DOCUMENTS

| | | |
|---|---|---|
| EP | 1474927 B1 | 8/2007 |
| JP | 2004-321603 | 11/2004 |
| JP | 2007-307395 | 11/2007 |
| JP | 2007-307396 | 11/2007 |
| JP | 2007-307397 | 11/2007 |
| KR | 1020060003050 A | 1/2006 |

* cited by examiner

*Primary Examiner* — Hung Dang
(74) *Attorney, Agent, or Firm* — Sherr & Jiang, PLLC

(57) ABSTRACT

A method of displaying images taken by a capsule endoscope and record media of storing program for carrying out that method, wherein the method comprises generating the capsule-endoscope image using image stream data transmitted from a capsule endoscope inserted into a living body, and generating a time bar corresponding to the generated capsule-endoscope image; displaying the generated capsule-endoscope image on a main-display area of a diagnosis screen; displaying at least one capture image on a sub-display area of the diagnosis screen when the capsule-endoscope image displayed on the main-display area is captured; and shifting the capture image on the sub-display area in such a way that the capture image is linked with a movement of a time slider positioned on the time bar, or moving the time slider on the time bar in such a way that the time slider is linked with a movement of the capture image.

8 Claims, 26 Drawing Sheets

METHOD OF DISPLAYING IMAGE TAKEN BY CAPSULE ENDOSCOPE AND RECORD MEDIA OF STORING PROGRAM FOR CARRYING OUT THAT METHOD

CROSS REFERENCE TO RELATED APPLICATIONS

This application claims the benefit of the Korean Patent Application Nos. P2008-0098111 filed on Oct. 7, 2008 and P2008-0113153 filed on Nov. 14, 2008, which are hereby incorporated by reference as if fully set forth herein.

BACKGROUND OF THE INVENTION

1. Field of the Invention

The present invention relates to a capsule endoscope, and more particularly, to a method of displaying images taken by a capsule endoscope.

2. Discussion of the Related Art

Recently, a capsule endoscope has been developed for observing a subject to be examined, for example, intestines of a living body without suffering pains, which can be used for medical diagnosis in the medical field. As this ingestible capsule endoscope is swallowed by a mouth of the living body until being naturally discharged out of the living body, the capsule endoscope traversing the internal of the living body takes intra-subject images, that is, images of stomach, small intestine, large intestine and etc. at a predetermined time rate. The images taken by the capsule endoscope are uploaded to a workstation through a receiving device and displayed on a display device through the use of diagnosis software installed in the workstation. An observer (which will be a doctor or nurse to make the medical diagnosis) makes the medical diagnosis by using the images taken by the capsule endoscope to write a report (medical diagnosis). At this time, the diagnosis software displays the images, which are taken in the time-sequential order by the capsule endoscope, on the display device at intervals of predetermined time.

In this case, the observer makes the report (medical diagnosis) after observing a large volume of the images taken by the capsule endoscope until the capsule endoscope is naturally discharged out of the living body.

However, the related art method of displaying the image taken by the capsule endoscope has the following disadvantages.

The observer can not search only the desired image among the large volume of the images taken by the capsule endoscope. Also, it is difficult to provide the observer with the correct recording time point of the image displayed on the display device.

SUMMARY OF THE INVENTION

Accordingly, the present invention is directed to a method of displaying images taken by a capsule endoscope and record media of storing program for carrying out that method that substantially obviates one or more problems due to limitations and disadvantages of the related art.

An aspect of the present invention is to provide a method of displaying images taken by a capsule endoscope and record media of storing program for carrying out that method, which is capable of improving diagnosis efficiency by displaying a time bar for providing entire time information about the images taken by the capsule endoscope and also displaying capture images captured by an observer among the images taken by the capsule endoscope, wherein a time slider positioned on the time bar is linked with the shift of the capture image.

Another aspect of the present invention is to provide a method of displaying images taken by a capsule endoscope and record media of storing program for carrying out that method which is capable of improving diagnosis efficiency by displaying the images taken by the capsule endoscope, and grouped capture images.

Additional features and aspects of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these and other advantages and in accordance with the purpose of the invention, as embodied and broadly described herein, a method of displaying a capsule-endoscope image comprises generating image stream data transmitted from a swallowable capsule endoscope inserted into a body, and generating a time bar corresponding to the generated capsule-endoscope image; displaying the generated capsule-endoscope image on a main-display area of a diagnosis screen; displaying at least one capture image on a sub-display area of the diagnosis screen when the capsule-endoscope image displayed on the main-display area is captured; and shifting the capture image on the sub-display area in such a way that the capture image is linked with a movement of a time slider positioned on the time bar, or moving the time slider on the time bar in such a way that the time slider is linked with a movement of the capture image.

At this time, the capture image is shifted in such a way that the capture image is linked with the movement of the time slider positioned on the time bar, time corresponding to a position of the moved time slider is detected, and the capture image are shifted so that other capture images having recording time being adjacent to the detected time are displayed on the sub-display area.

Also, the time slider is moved in such a way that the time slider is linked with the shift of the capture image, recording time of the reference capture image among the shifted capture images is detected, and the time slider of the time bar is moved to be corresponding to the detected recording time of the reference capture image.

When there is an observer's request for changing the size of the sub-display area, the method further comprises enlarging the sub-display area to display the capture images on the enlarged sub-display area, or reducing the enlarged sub-display area to the original size of the sub-display area to display the capture images on the sub-display area.

The capture images displayed on the enlarged sub-display area are sequentially aligned according to the recording time so as to have a matrix configuration, wherein the matrix configuration may be formed in such a way that the first column is provided with the capture images having the earliest recording time among the capture images provided in each row, or in such a way that the first row is provided with the capture images having the earliest recording time among the capture images provided in each column.

In addition, the method further comprises storing diagnosis information about the capture image; displaying the capture image including the diagnosis information on the sub-display area of the diagnosis screen; and providing the observer with the diagnosis information selected by the observer.

The diagnosis information includes a first diagnosis information icon corresponding to text information about a diagnosis result of the observer, and a second diagnosis information icon corresponding to sound information about the capture image.

The process of providing the observer with the diagnosis information comprises displaying the text information on the main-display area or an additional popup window in response to the first diagnosis information icon selected by the observer; and displaying the sound information in response to the second diagnosis information icon selected by the observer.

In another aspect of the present invention, a method of displaying a capsule-endoscope image comprises generating the capsule-endoscope image using stream data transmitted from a capsule endoscope inserted into a living body, and displaying the generated capsule-endoscope image on a main-display area of a diagnosis screen; generating a plurality of capture image bags by grouping capture images when the capsule-endoscope image displayed on the main-display area is captured; and displaying the plurality of capture image bags on a sub-display area of the diagnosis screen.

In another aspect of the present invention, a diagnosis screen of a capsule-endoscope image for displaying an in-vivo image photographed by a capsule endoscope comprises a main-display area for displaying the in-vivo image at a predetermined playing rate; and a sub-display area for displaying a plurality of capture image bags formed by grouping capture images from the in-vivo image displayed on the main-display area, wherein at least one of the capture images grouped is displayed on the capture image bag.

It is to be understood that both the foregoing general description and the following detailed description of the present invention are representative and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings.

DETAILED DESCRIPTION OF THE INVENTION

Reference will now be made in detail to the preferred embodiments of the present invention, examples of which are illustrated in the accompanying drawings. Wherever possible, the same reference numbers will be used throughout the drawings to refer to the same or like parts.

Hereinafter, a method of displaying an image taken by a capsule endoscope according to the present invention and record media of storing program for carrying out the method will be explained with reference to the accompanying drawings.

Figure 1:
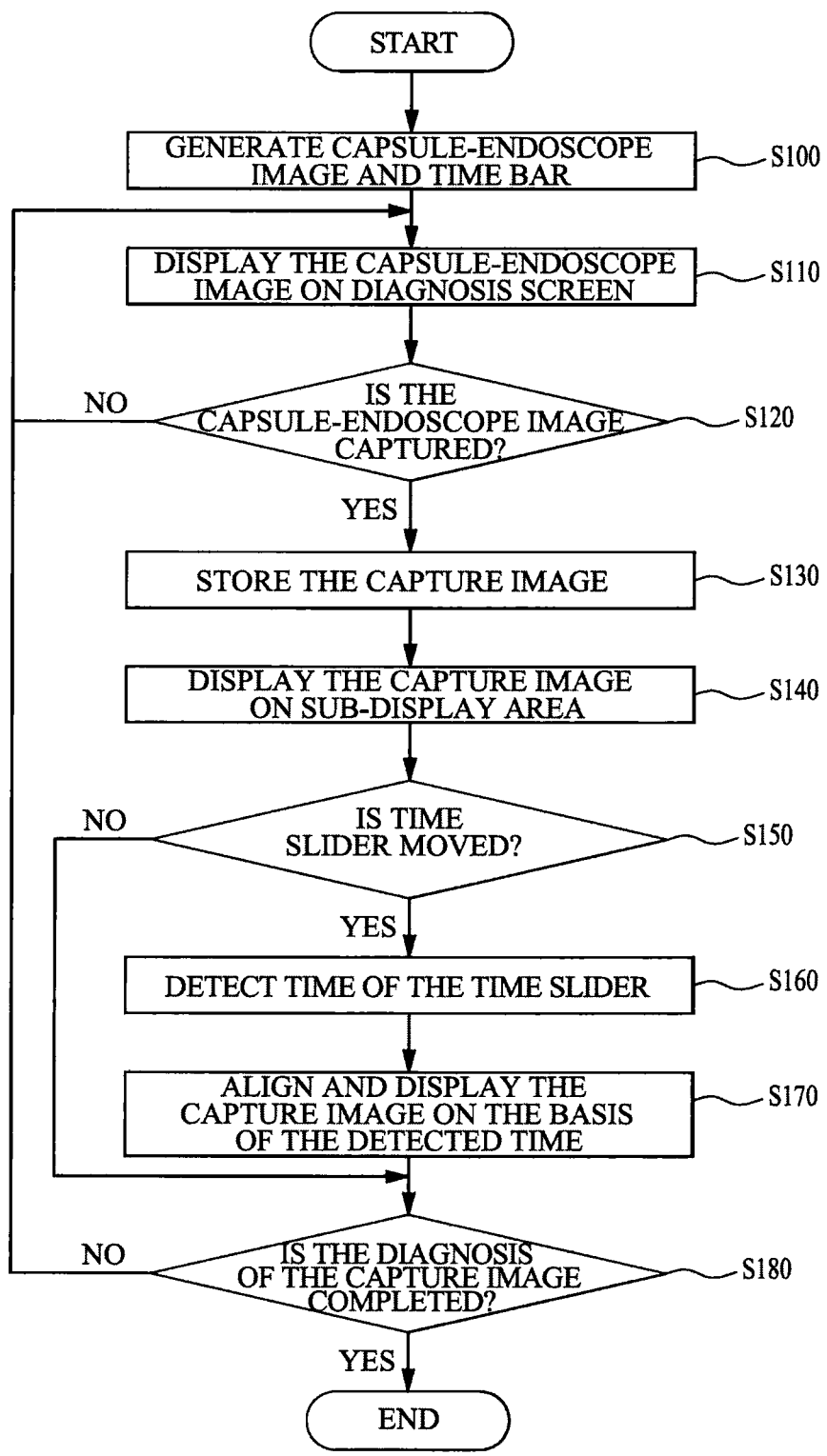
FIG. 1 is a flowchart illustrating a method of displaying an image taken by a capsule endoscope according to the first embodiment of the present invention.

FIG. 1 is a flowchart illustrating a method of displaying an image taken by a capsule endoscope according to the first embodiment of the present invention.

A method of displaying an image taken by a capsule endoscope according to the first embodiment of the present invention will be explained with reference to FIG. 1.

By swallowing an ingestible capsule endoscope (not shown), the capsule endoscope is inserted into a subject to be examined, i.e., living body. Then, an image taken by the capsule endoscope (hereinafter, referred to as 'capsule-endoscope image') is generated through the use of image stream data transmitted from the capsule endoscope inserted into the inside of the subject, and a time bar corresponding to the entire capsule-endoscope image is generated in step S100. In this case, the image stream data may be stored in and provided from a storing device (not shown) of a workstation (not shown) through a receiving device which receives the image stream data transmitted from the capsule endoscope, or may be directly provided from the receiving device in real-time.

Figure 2:
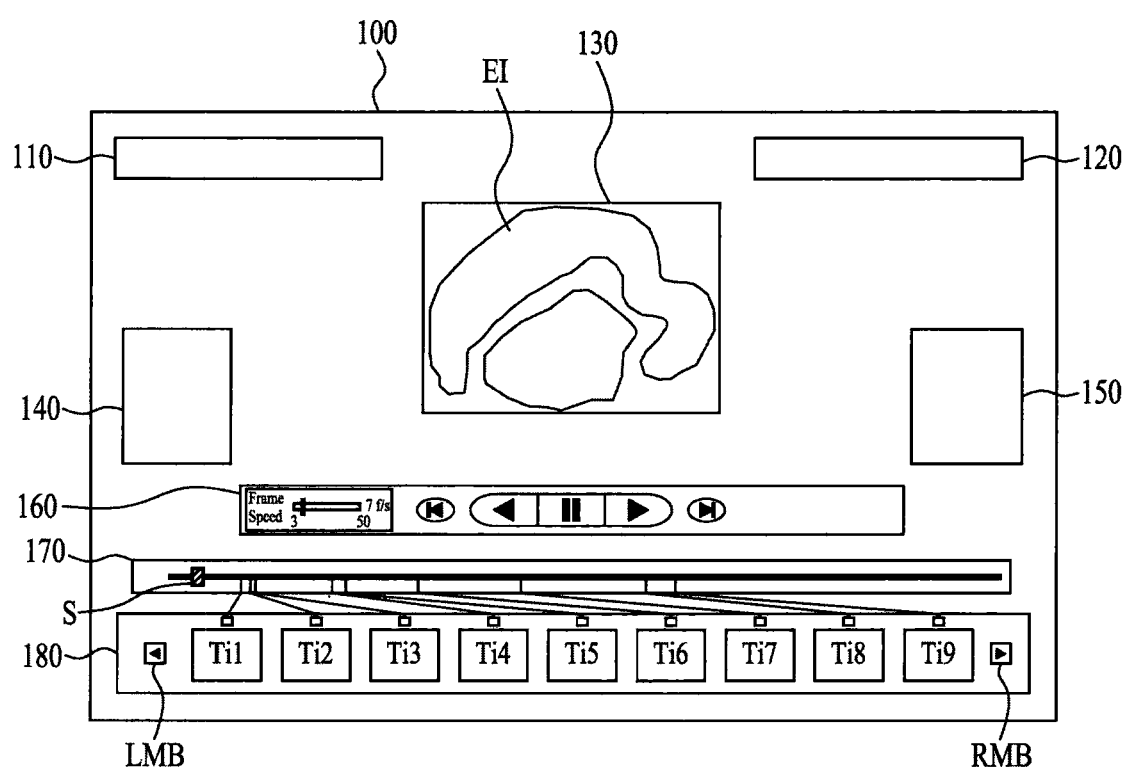
FIG. 2 illustrates a diagnosis screen in the image displaying method according to the first embodiment of the present invention.

As shown in FIG. 2, the generated image (E1) is displayed on a diagnosis screen 100 of a display device (not shown) in step S110.

At this time, the diagnosis screen 100 includes a program tool menu 110, a view/mode menu 120, a main-display area 130, a capsule-endoscope position display area 140, a comparative image display area 150, a play menu 160, a time bar display area 170, and a sub-display area 180.

The program tool menu 110 may include menu icons for conversion into a screen of controlling the receiving device; for conversion into a data screen of an examinee to be examined; for conversion into a screen of checking the capsule-endoscope image of the selected examinee; for conversion into a screen of writing a report (medical diagnosis) for the selected examinee; for conversion into a screen of extracting the capsule-endoscope image of the selected examinee; and for conversion into a screen for a backup of the capsule-endoscope image of the selected examinee.

The view/mode menu 120 may include menu icons for selecting 2D or 3D mode; for displaying the capsule-endoscope images as one; for displaying the capsule-endoscope image as two; for displaying the capsule-endoscope image as four; for enlarging the capsule-endoscope image; for playing the entire capsule-endoscope images; for selectively playing the capsule-endoscope images; and for playing some area suspected to have bloodstains.

The generated capsule-endoscope image (E1) is displayed on the main-display area 130. At this time, a display rate of the capsule-endoscope image (E1) displayed on the main-display area 130 may be changed based on a preset frame rate. The capsule-endoscope image (E1) is displayed on the main-display area 130 according to the selected menu icon from the view/mode menu 120.

The capsule-endoscope position display area 140 displays information about the position of the capsule endoscope traversing the inside of the examinee to be examined.

The comparative image display area 150 displays a reference capsule-endoscope image, to thereby compare the capsule-endoscope image of the selected examinee with the displayed reference capsule-endoscope image.

The play menu 160 may include menu icons for adjusting the frame rate of the capsule-endoscope image (E1) displayed on the main-display area 130; for forward playing of the image; for reverse playing of the image; for fast forward playing of the image; for fast reverse playing of the image; for stopping of the image playing; for temporarily stopping of the image playing; for the shift to the prior capture image; for the shift to the next capture image; for capturing of current capsule-endoscope image; and for marking the current capsule-endoscope image.

On the time bar display area 170, information about time and distance of the entire capsule-endoscope image (E1) is displayed as a bar type, which includes a time slider (S) which displays the position corresponding to the information about the time and distance of the current capsule-endoscope image, displayed on the main-display area 130. The time slider (S) can be freely controlled by an observer. The capsule-endoscope image (E1) corresponding to the position of the time slider (S) is displayed on the main-display area 130.

The sub-display area 180 displays the capture image which corresponds to the capsule-endoscope image captured by the observer. That is, the observer diagnoses the examinee's diseases of bleeding, cancer, polyp, ulcer, and erosion by observing the capsule-endoscope image (E1) displayed on the main-display area 130; and captures the corresponding image (E1) if needed. Accordingly, the capsule-endoscope image (E1) captured by the observer is stored as the capture image, and also sequentially displayed on the sub-display area 180.

Each capture image (Ti) displayed on the sub-display area 180 is linked with the time bar of the time bar display area 170. This enables the observer to get the information about the time at which each capture image (Ti) is photographed by the capsule endoscope.

At one side of the sub-display area 180, there is a first moving button (LMB) for shifting the capture images (Ti) leftward. At the other side of the sub-display area 180, there is a second moving button (RMB) for shifting the capture images (Ti) rightward. Thus, the observer can shift the capture images (Ti) displayed on the sub-display area 180 leftward or rightward through the use of first or second moving button (LMB or RMB).

In FIG. 1, it is checked whether or not the capsule-endoscope image (E1) displayed on the main-display area 130 is captured by the observer in step S120.

If the capsule-endoscope image (E1) displayed on the main-display area 130 is captured by the observer in step S120 (that is, 'yes' in step S120), the capsule-endoscope image (E1) displayed on the main-display area 130 is captured and then stored as the capture image (Ti) in step S130.

If the capsule-endoscope image (E1) displayed on the main-display area 130 is not captured by the observer in step S120 (that is, 'no' in S120), the next capsule-endoscope image (E1) is displayed on the main-display area 130 by the aforementioned step S110.

The stored capture images (Ti) are sequentially displayed on the sub-display area 180 in step S140.

Then, it is checked whether or not the time slider (S) is moved by the observer in step S150.

If the time slider (S) is moved by the observer in step S150 (that is, 'yes' in step S150), the time corresponding to the moved time slider (S) is detected in step S160.

Then, the capture images (Ti) are aligned on the basis of the detected time of the time slider (S), and are then displayed in step S170.

Figure 3A:
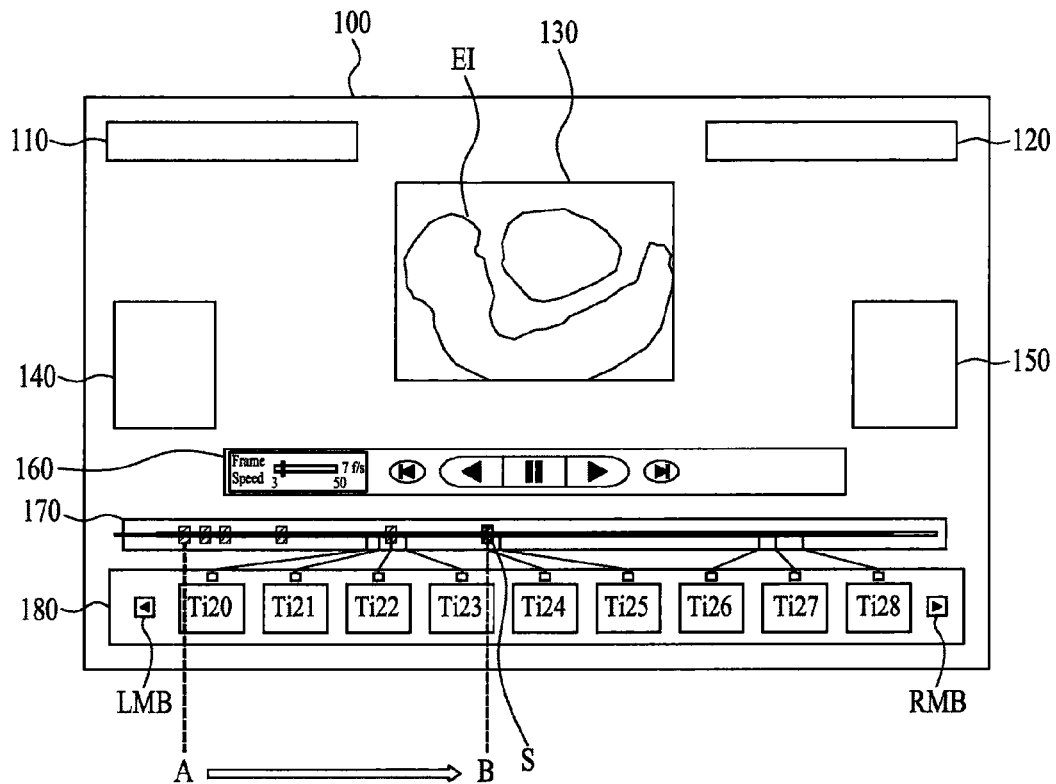
FIGS. 3A and 3B illustrate a shift of capture image in the image displaying method according to the first embodiment of the present invention.

According to one embodiment of the present invention, as shown in FIG. 3A, if the observer moves the time slider (S) from a first point (A) to a second point (B) on the time bar, the capture image (Ti) is shifted leftward by the movement of the time slider (S) since the capture image (Ti) displayed on the sub-display area 180 is linked with the movement of the time slider (S), whereby other capture images (Ti) being adjacent to the time of the time slider (S) are aligned and displayed on the sub-display area 180. For example, if the time slider (S) is positioned at the $24^{th}$ capture image (Ti24), the $24^{th}$ capture image (Ti24) is displayed at the center of the sub-display area 180, and the prior and next capture images for the current $24^{th}$ capture image (Ti24) are aligned and displayed in sequence.

Figure 3B:
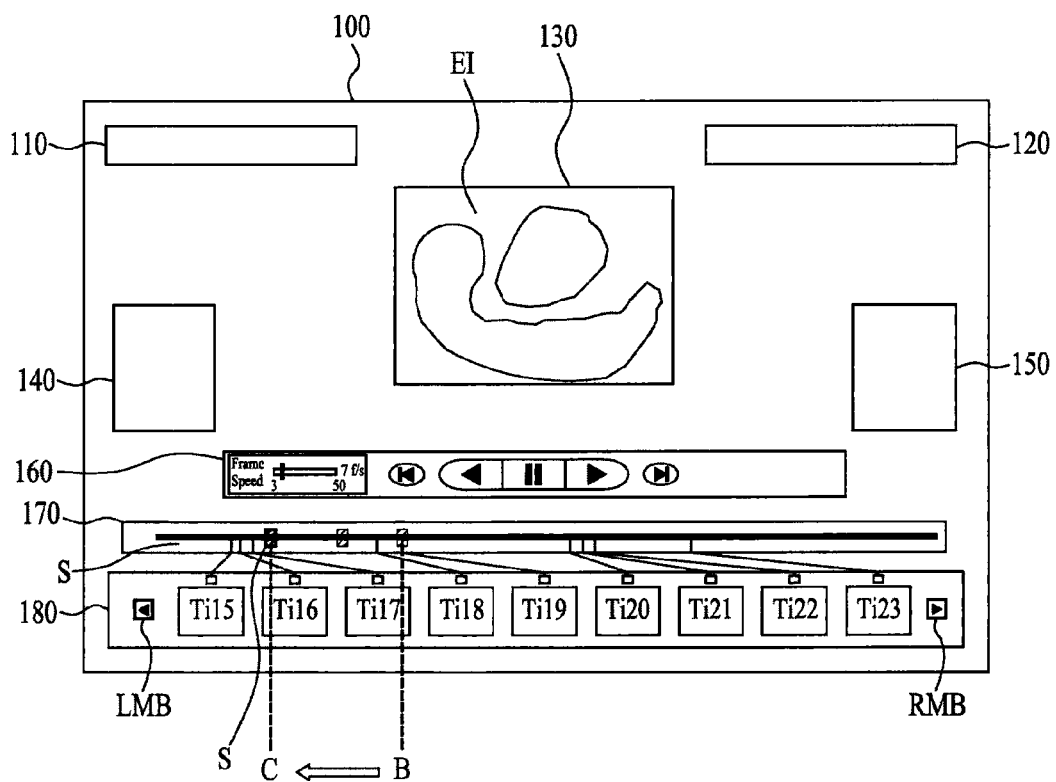

According to another embodiment of the present invention, as shown in FIG. 3B, if the observer moves the time slider (S) from a second point (B) to a first point (C), the capture image (Ti) is moved rightward by the movement of the time slider (S) since the capture image (Ti) displayed on the sub-display area 180 is linked with the movement of the time slider (S), whereby other capture images (Ti) being adjacent to the time of the time slider (S) are aligned and displayed on the sub-display area 180. For example, if the time slider (S) is positioned at the $19^{th}$ capture image (Ti19), the $19^{th}$ capture image (Ti19) is displayed at the center of the sub-display area 180, and the prior and next capture images for the current 19$^{th}$ capture image (Ti19) are aligned and displayed in sequence.

It is checked whether or not the observer completes the diagnosis of the capsule-endoscope image (E1) in step S180.

If the observer completes the diagnosis of the capsule-endoscope image (E1) in step S180, it is determined that the diagnosis of the capsule-endoscope image (E1) is completed by the observer.

If the diagnosis of the capsule-endoscope image (E1) is not completed in step S180, the aforementioned steps S110 to S170 are performed repetitively.

If the time slider (S) is not moved by the observer in step S150 (that is, 'no' in step S150), the aforementioned step S180 is performed.

In the method of displaying the capsule-endoscope image according to the first embodiment of the present invention, the movement of the capture image (Ti) is linked with the movement of the time slider (S) according to the observer's operation, so that the capture image (Ti) corresponding to the observer's interest is provided to the observer, thereby improving diagnosis efficiency.

Figure 4:
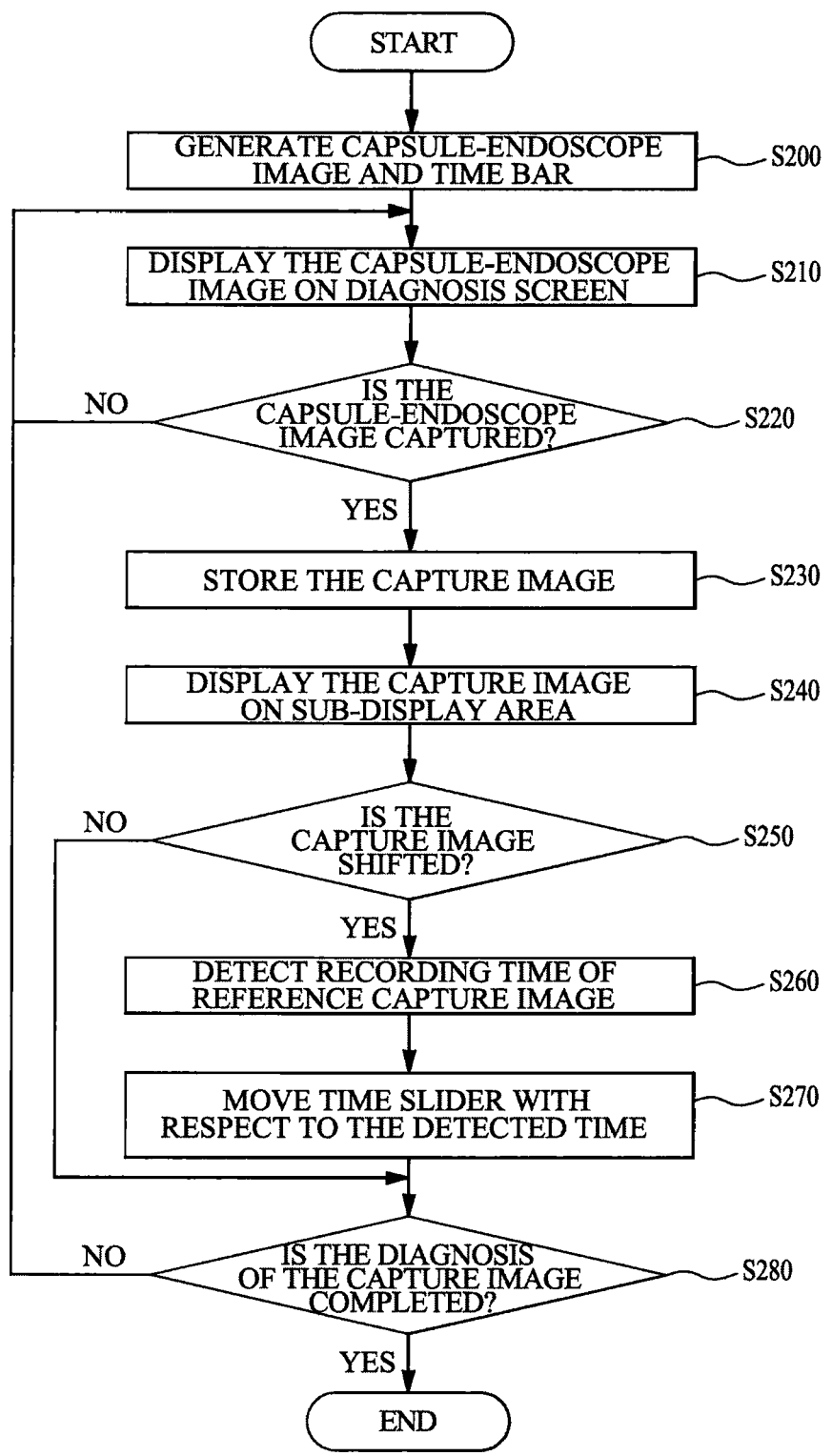
FIG. 4 is a flowchart illustrating a method of displaying an image taken by a capsule endoscope according to the second embodiment of the present invention.

FIG. 4 is a flowchart illustrating a method of displaying an image taken by a capsule endoscope according to the second embodiment of the present invention.

A method of displaying an image taken by a capsule endoscope according to the second embodiment of the present invention will be explained with reference to FIG. 4.

By swallowing a capsule endoscope (not shown), the capsule endoscope is inserted into a subject to be examined, i.e., living body. Then, an image taken by the capsule endoscope (hereinafter, referred to as 'capsule-endoscope image') is generated through the use of image stream data transmitted from the capsule endoscope inserted into the inside of the subject, and a time bar corresponding to the entire capsule-endoscope image is generated in step S200. In this case, the image stream data may be stored in and provided from a storing device (not shown) of a workstation (not shown) through a receiving device which receives the image stream data transmitted from the capsule endoscope, or may be directly provided from the receiving device in real-time.

Figure 5:
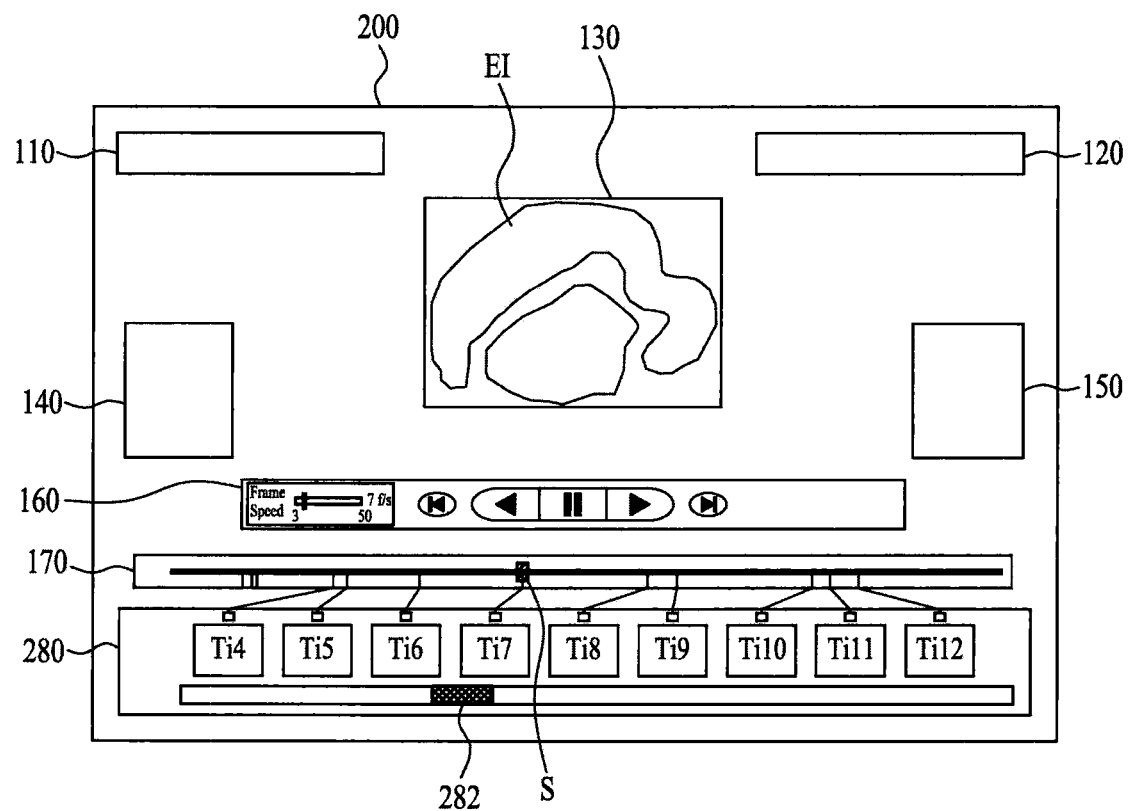
FIG. 5 illustrates a diagnosis screen in the image displaying method according to the second embodiment of the present invention.

As shown in FIG. 5, the generated image (E1) is displayed on a diagnosis screen 200 of a display device in step S210.

At this time, the diagnosis screen 200 includes a program tool menu 110, a view/mode menu 120, a main-display area 130, a capsule-endoscope position display area 140, a comparative image display area 150, a play menu 160, a time bar display area 170, and a sub-display area 280. Except the sub-display area 280, the diagnosis screen 200 according to the second embodiment of the present invention is identical in structure to the diagnosis screen 100 according to the first embodiment of the present invention, whereby the detailed explanation for the same structures will be omitted.

A capture image (Ti) captured by the observer is displayed on the sub-display area 280 in such a way that the capture image (Ti) is linked with the time bar display area 170.

The sub-display area 280 includes a scroll bar 282 for shifting the capture images (Ti) leftward or rightward. Accordingly, the observer can freely observe or examine the desired capture image (Ti) by moving the scroll bar 282 leftward or rightward.

In FIG. 4, it is checked whether or not the capsule-endoscope image (E1) displayed on the main-display area 130 is captured by the observer in step S220.

If the capsule-endoscope image (E1) displayed on the main-display area 130 is captured by the observer in step S220 (that is, 'yes' in step S220), the capsule-endoscope image (E1) displayed on the main-display area 130 is captured and is then stored as the capture image (Ti) in step S230.

If the capsule-endoscope image (E1) displayed on the main-display area 130 is not captured by the observer in step S220 (that is, 'no' in step S220), the next capsule-endoscope image (E1) is displayed on the main-display area 130 by the aforementioned step S210.

The stored capture images (Ti) are sequentially displayed on the sub-display area 280 in step S240.

Then, it is checked whether or not the time slider (Si) is moved by the observer in step S250.

If the scroll bar 282 is moved by the observer in step S250 (that is, 'yes' in step S250), the recording time of the reference capture image (Ti) displayed at a reference point of the sub-display area 280 is detected in step S260. At this time, the reference point of the sub-display area 280 may be the central point of the sub-display area 280.

Then, the time slider (S) is moved on the basis of the recording time of the detected capture image (Ti) in step S270.

Figure 6A:
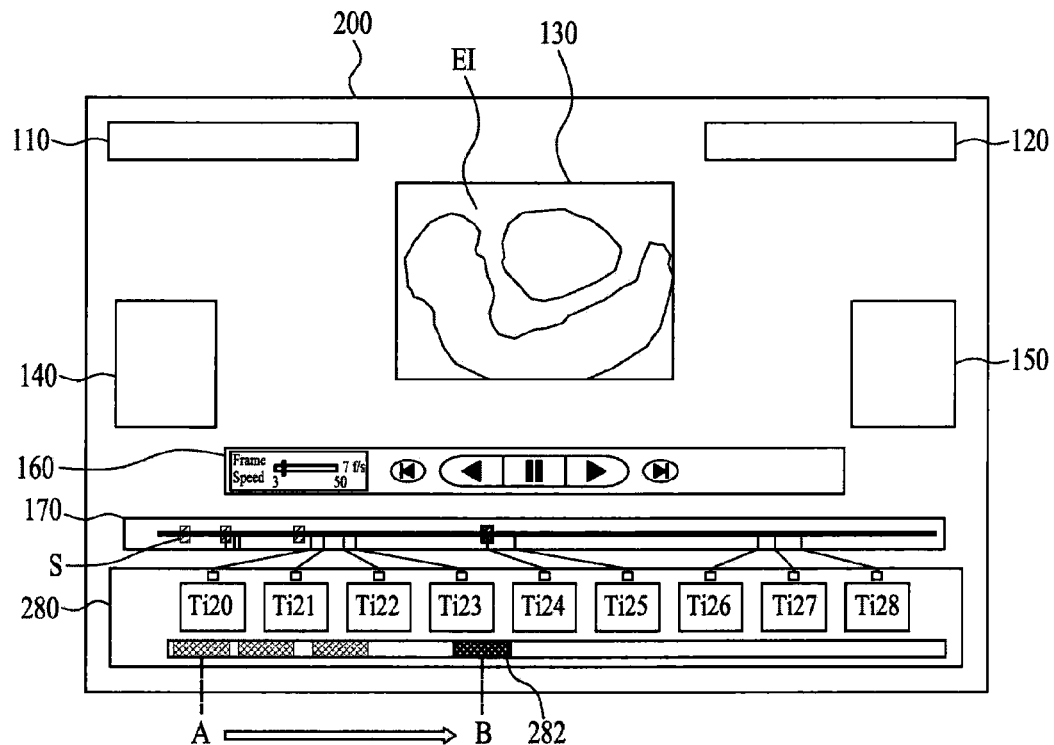
FIGS. 6A and 6B illustrate a movement of time slider in the image displaying method according to the first embodiment of the present invention.

According to one embodiment of the present invention, as shown in FIG. 6A, if the observer moves the scroll bar 282 from a first point (A) to a second point (B), the time slider (S) is moved rightward by the movement of the scroll bar 282 since the time slider (S) is linked with the movement of the scroll bar 282, whereby the time slider (S) is moved to be positioned at the predetermined portion of the time bar corresponding to the recording time of the reference capture image (Ti) displayed on the sub-display area 180. For example, if the reference capture image (Ti) is the 24$^{th}$ capture image (Ti24) according to the scroll of the scroll bar 282, the time slider (S) may be moved to the predetermined portion of the time bar corresponding to the recording time of the 24$^{th}$ capture image (Ti24).

Figure 6B:
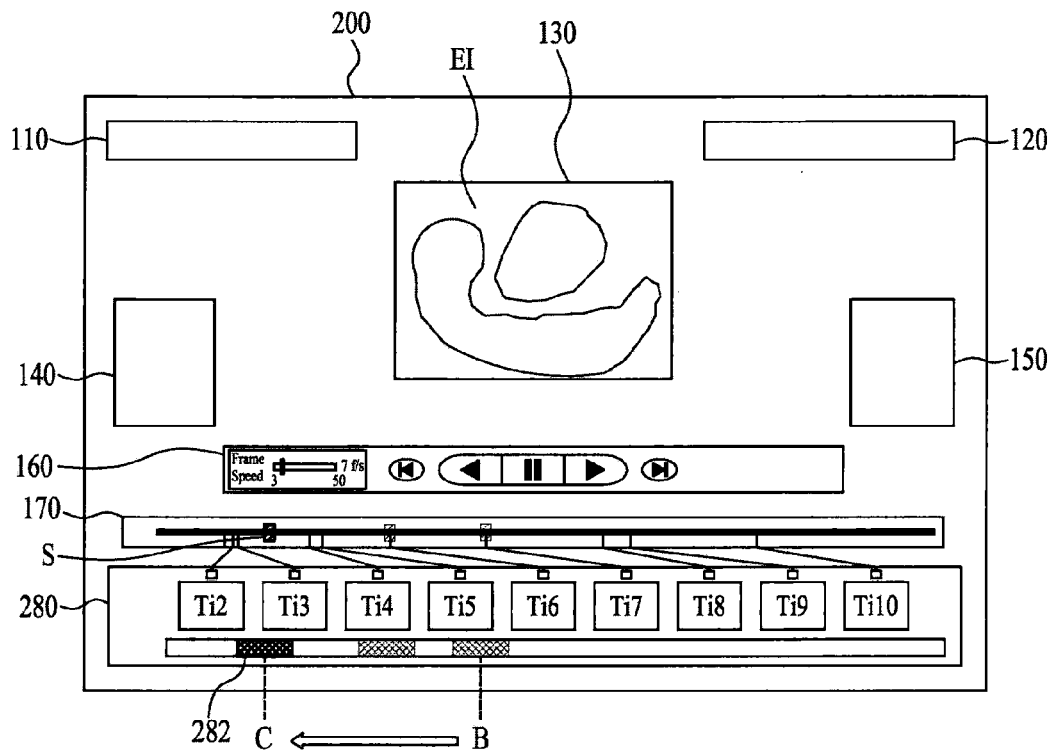

According to another embodiment of the present invention, as shown in FIG. 6B, if the observer moves the scroll bar 282 from a second point (B) to a third point (C), the time slider (S) is moved rightward by the movement of the scroll bar 282 since the time slider (S) is linked with the movement of the scroll bar 282, whereby the time slider (S) is moved to be positioned at the predetermined portion of the time bar corresponding to the recording time of the reference capture image (Ti) displayed on the sub-display area 180. For example, if the reference capture image (Ti) is the 6$^{th}$ capture image (Ti6) according to the scroll of the scroll bar 282, the time slider (S) may be moved to the predetermined portion of the time bar corresponding to the recording time of the 6$^{th}$ capture image (Ti6).

It is checked whether or not the observer completes the diagnosis of the capsule-endoscope image (E1) in step S280.

If the diagnosis of the capsule-endoscope image (E1) is completed by the observer in step S280, it is determined that the diagnosis of the capsule-endoscope image (E1) is completed by the observer.

If the diagnosis of the capsule-endoscope image (E1) is not completed by the observer in step S280, the aforementioned steps S210 to S270 are performed repetitively until completing the diagnosis.

In the meantime, if the scroll bar 282 is not moved by the observer in step S250 (that is, 'no' in step S250), the aforementioned step S280 is performed.

In the method of displaying the capsule-endoscope image according to the second embodiment of the present invention, the movement of the time slider (S) is linked with the movement of the capture image (Ti) according to the observer's operation, so that the time information corresponding to the capture image (Ti) moved by the movement of the time slider (S) is provided to the observer, thereby improving diagnosis efficiency.

The method of displaying the capsule-endoscope image according to the second embodiment of the present invention discloses that the time slider (S) is moved by the movement of the scroll bar 282 while being linked with the scroll bar 282 of the sub-display area 280 of the diagnosis screen 200. However, it is not limited to this structure. Selectively, the time slider (S) may be linked with the movement of the capture image (Ti) so that the time slider (S) may be moved by the movement of the capture image (Ti). That is, as shown in FIG. 2, the time slider (S) may be moved by the movement of the capture image (Ti) linked therewith through the use of first or second moving button (LMB, RMB) of the sub-display area 180.

Figure 7:
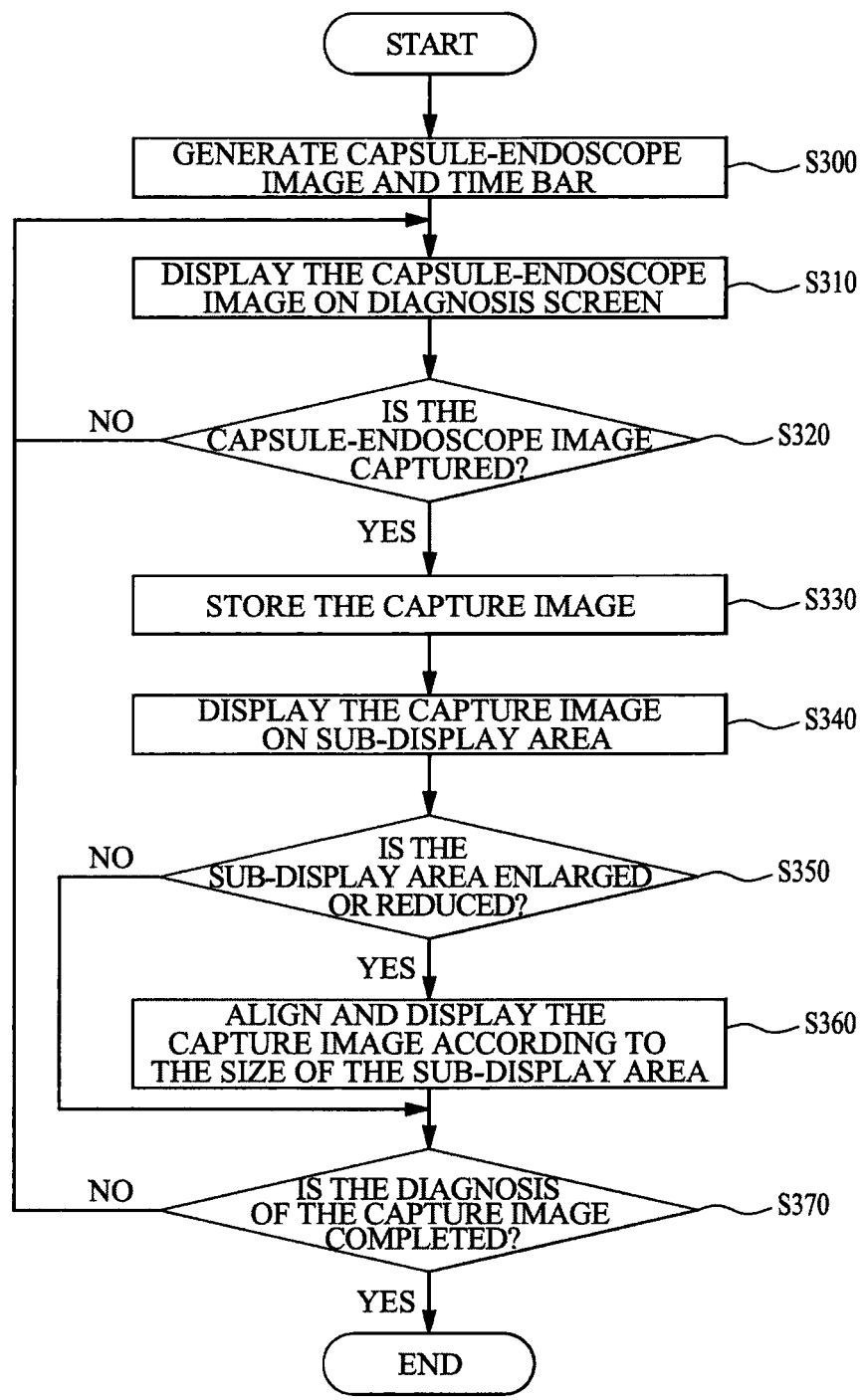
FIG. 7 is a flowchart illustrating a method of displaying an image taken by a capsule endoscope according to the third embodiment of the present invention.

FIG. 7 is a flowchart illustrating a method of displaying an image taken by a capsule endoscope according to the third embodiment of the present invention.

A method of displaying an image taken by a capsule endoscope according to the third embodiment of the present invention will be explained with reference to FIG. 7.

By swallowing a capsule endoscope (not shown), the capsule endoscope is inserted into a subject to be examined, i.e., living body. Then, an image taken by the capsule endoscope (hereinafter, referred to as 'capsule-endoscope image') is generated through the use of image stream data transmitted from the capsule endoscope inserted into the inside of the subject, and a time bar corresponding to the entire capsule-endoscope image is generated in step S300. In this case, the image stream data may be stored in and provided from a storing device (not shown) of a workstation (not shown) through a receiving device which receives the image stream data transmitted from the capsule endoscope, or may be directly provided from the receiving device in real-time.

Figure 8:
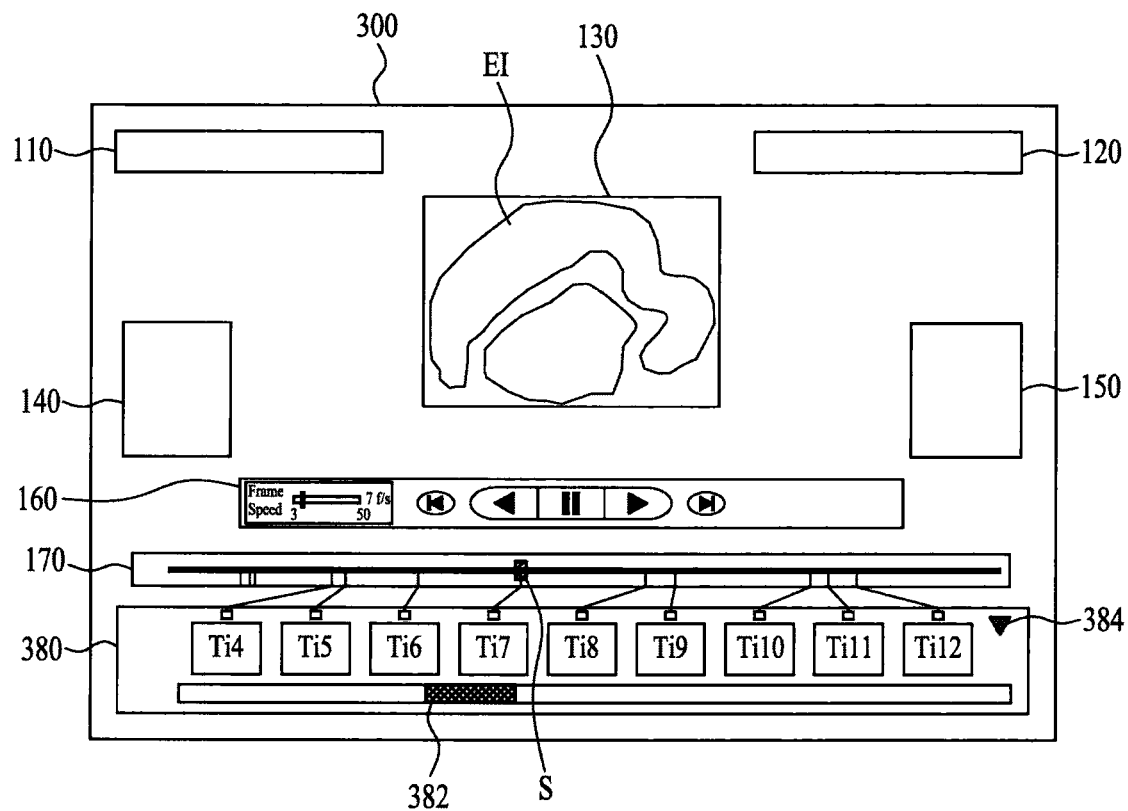
FIG. 8 illustrates a diagnosis screen in the image displaying method according to the third embodiment of the present invention.

As shown in FIG. 8, the generated image (E1) is displayed on a diagnosis screen 300 of a display device in step S310.

At this time, the diagnosis screen 300 includes a program tool menu 110, a view/mode menu 120, a main-display area 130, a capsule-endoscope position display area 140, a comparative image display area 150, a play menu 160, a time bar display area 170, and a sub-display area 380. Except the sub-display area 380, the diagnosis screen 300 according to the third embodiment of the present invention is identical in structure to the diagnosis screen 100 according to the first embodiment of the present invention, whereby the detailed explanation for the same structures will be omitted.

A capture image (Ti) captured by the observer is displayed on the sub-display area 380 in such a way that the capture image (Ti) is linked with the time bar display area 170.

The sub-display area 380 includes a scroll bar 382 for shifting the capture image (Ti) leftward or rightward; and an enlarging/reducing button 384 displayed at one side thereof.

As explained with reference to the second embodiment of the present invention, the scroll bar 382 is moved according to the observer's operation. The capture images (Ti) are shifted in such a way that the capture images (Ti) are linked with the movement of the scroll bar 382.

The enlarging/reducing button 384 corresponds to a menu to enlarge or reduce the sub-display area 380 in response to the observer's operation. Through the enlarging/reducing button 384, the observer can enlarge or reduce the sub-display area 380.

In FIG. 7, it is checked whether or not the capsule-endoscope image (E1) displayed on the main-display area 130 is captured by the observer in step S320.

If the capsule-endoscope image (E1) displayed on the main-display area 130 is captured by the observer in step S320 (that is, 'yes' in step S320), the capsule-endoscope image (E1) displayed on the main-display area 130 is captured and is then stored as the capture image (Ti) in step S330.

If the capsule-endoscope image (E1) displayed on the main-display area 130 is not captured by the observer in step S320 (that is, 'no' in step S320), the next capsule-endoscope image (E1) is displayed on the main-display area 130 by the aforementioned step S310.

The stored capture images (Ti) are sequentially displayed on the sub-display area 380 in step S340.

Then, it is checked whether or not the sub-display area 380 is enlarged by the observer and whether or not the enlarged sub-display area 380 is reduced in step S350.

If the sub-display area 380 is enlarged or the enlarged sub-display area 380 is reduced by the observer in step S350 (that is, 'yes' in step S350), the capture image (Ti) is aligned and displayed on the basis of the size of the sub-display area 380 in step S360.

Then, it is checked whether or not the diagnosis of the capsule-endoscope image (E1) is completed by the observer in step S370.

If the diagnosis of the capsule-endoscope image (E1) is completed by the observer in step S370, it is determined that the diagnosis of the capsule-endoscope image (E1) is completed by the observer.

If the diagnosis of the capsule-endoscope image (E1) is not completed by the observer in step S370, the aforementioned steps S310 to S360 are performed repetitively until completing the diagnosis.

If the observer does not enlarge the sub-display area 380 or does not reduce the enlarged sub-display area 380 (that is, 'no' in step S350), the aforementioned step S370 is performed.

Figure 9:
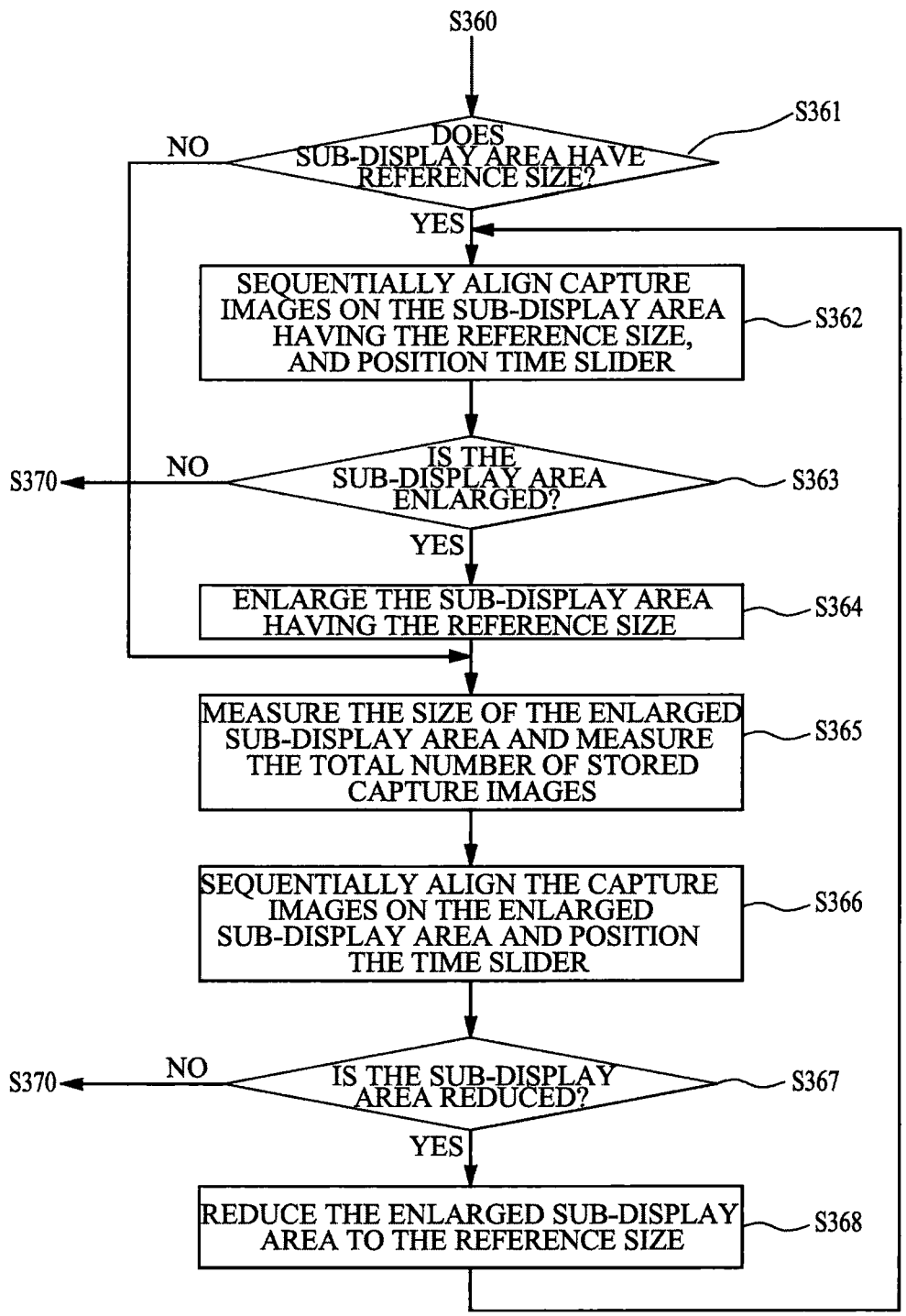
FIG. 9 is a flowchart illustrating a method of displaying a capture image on a sub-display area of FIG. 7.

FIG. 9 is a flowchart illustrating a method of aligning and displaying the capture image according to the size of the sub-display area shown in FIG. 7.

A method of aligning and displaying the capture image according to the size of the sub-display area will be explained with reference to FIG. 9 in conjunction with FIGS. 7 and 8.

First, it is checked whether or not the sub-display area 380 has a reference size in step S361.

If the sub-display area 380 has the reference size in step S361 (that is, 'yes' in the step S361), as shown in FIG. 8, the capture images (Ti) are sequentially aligned in the sub-display area 380 with the reference size, and the time slider (S) is moved to be positioned at the recording time of the reference capture image (Ti8) displayed on the sub-display area 380 with the reference size in step S362.

Then, it is checked whether or not the observer enlarges the sub-display area 380 with the reference size by operating the enlarging/reducing button 384 in step S363.

Figure 10:
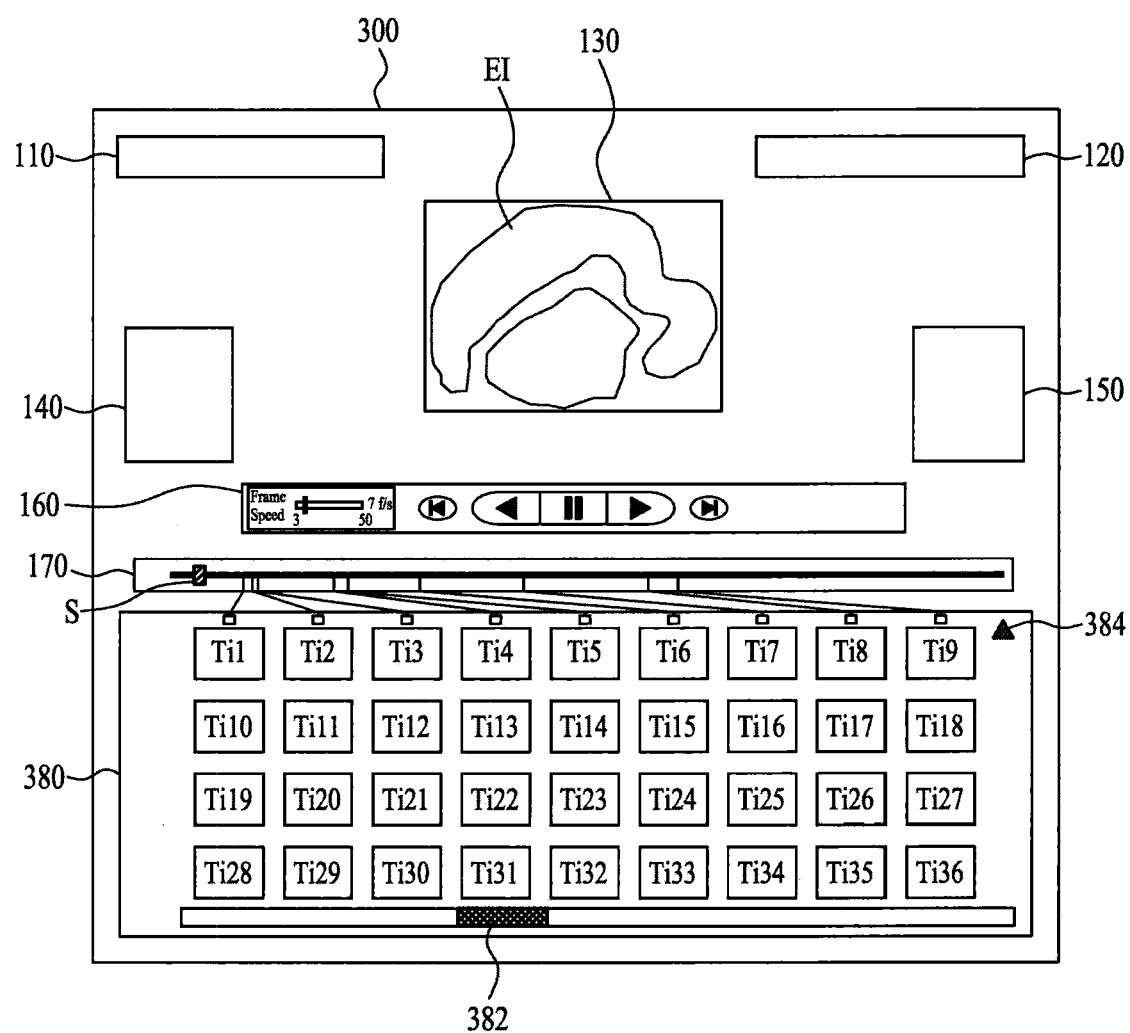
FIG. 10 illustrates an enlargement of sub-display area in the image displaying method according to the third embodiment of the present invention.

If the observer enlarges the sub-display area 380 with the reference size in step S363 (that is, 'yes' in step S363), as shown in FIG. 10, the sub-display area 380 with the reference size is enlarged in step S364.

Then, the size of the enlarged sub-display area is measured, and the total number of the capture images stored by the observer is measured in step S365.

Then, the capture images (Ti) are displayed in a matrix configuration through the sequential alignment on the basis of the size of the enlarged sub-display area 380; and the time slider (S) is moved to be positioned at the predetermined portion corresponding to the recording time of the reference capture image (Ti) among the aligned capture images (Ti) in step S366. At this time, the reference capture image (Ti) may correspond to the capture image (Ti) displayed at the uppermost central portion of the sub-display area 380 among the capture images (Ti) displayed in the matrix configuration on the sub-display area 380.

If the sub-display area 380 with the reference size is not enlarged by the observer in step S363 (that is, 'no' in step S363), the aforementioned step S370 of FIG. 7 is performed.

Then, it is checked whether or not the enlarged sub-display area 380 is reduced by the observer through the enlarging/reducing button 384 in step S367.

If the enlarged sub-display area 380 is reduced by the observer in step S367 (that is, 'yes' in step S367), as shown in FIG. 8, the enlarged sub-display area is reduced to the reference size in step s368, and then the aforementioned steps S362 to S367 are performed in sequence.

If the enlarged sub-display area 380 is not reduced by the observer in step S367 (that is, 'no' in step S367), the aforementioned step S370 of FIG. 7 is performed.

The method of displaying the capsule-endoscope image according to the third embodiment of the present invention can enlarge the sub-display area 380 according to the observer's operation, whereby more capture images (Ti) can be displayed on the enlarged sub-display area 380, to thereby improve diagnosis efficiency.

In the third embodiment of the present invention, the capture images (Ti) displayed on the enlarged sub-display area can be arranged and displayed in various configurations.

According to one embodiment of the present invention, as shown in FIG. 10, the enlarged sub-display area may be provided with the capture images (Ti1 to Tin) arranged in 'N×M' matrix configuration according to the number of capture images (Ti1 to Tin), wherein the capture images (Ti1 to Tin) are sequentially arranged along the row direction according to the recording time. In the first column, there are the capture images (Ti1, Ti10, Ti19, Ti28) having the earliest recording time among the capture images provided in each row. For example, the capture images (Ti1 to Tin) may be arranged in '4×9' matrix configuration.

Figure 11A:
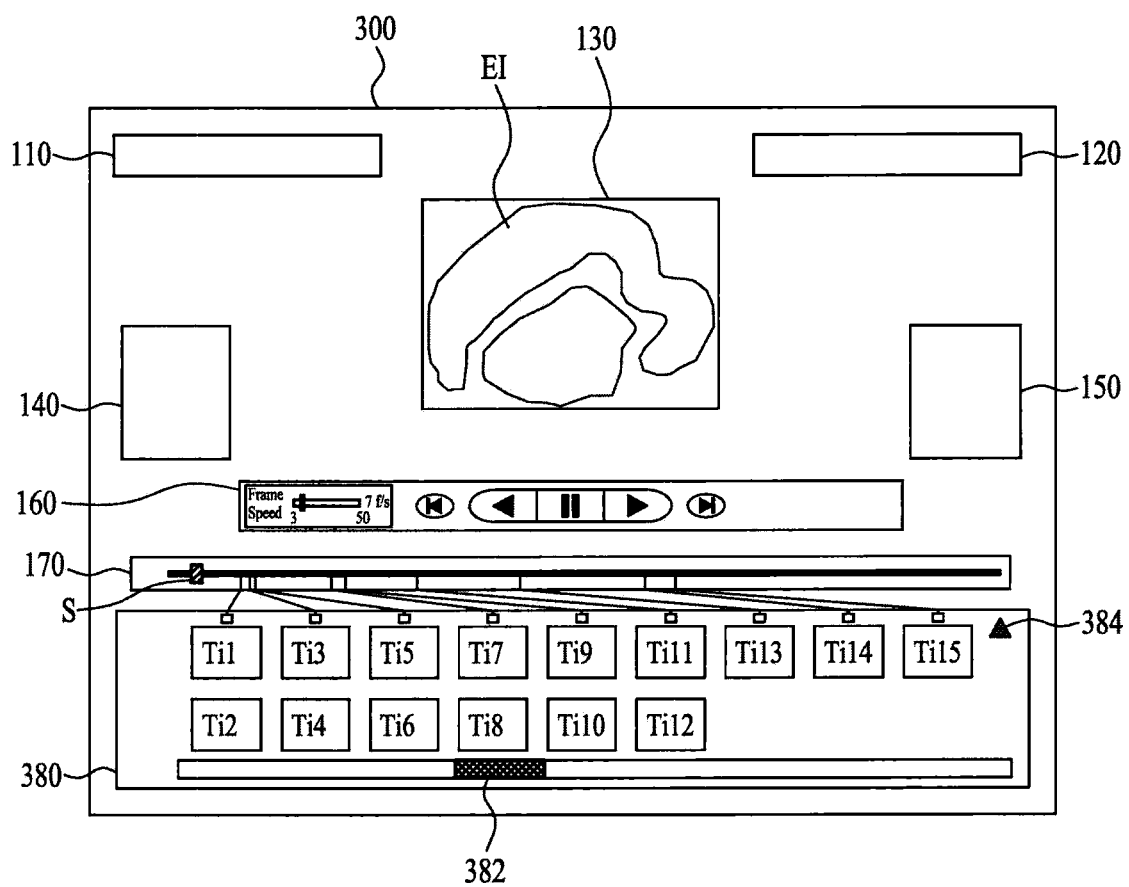
FIGS. 11A to 11C illustrate various methods of displaying a capture image on the enlarged sub-display area of FIG. 10.
Figure 11B:
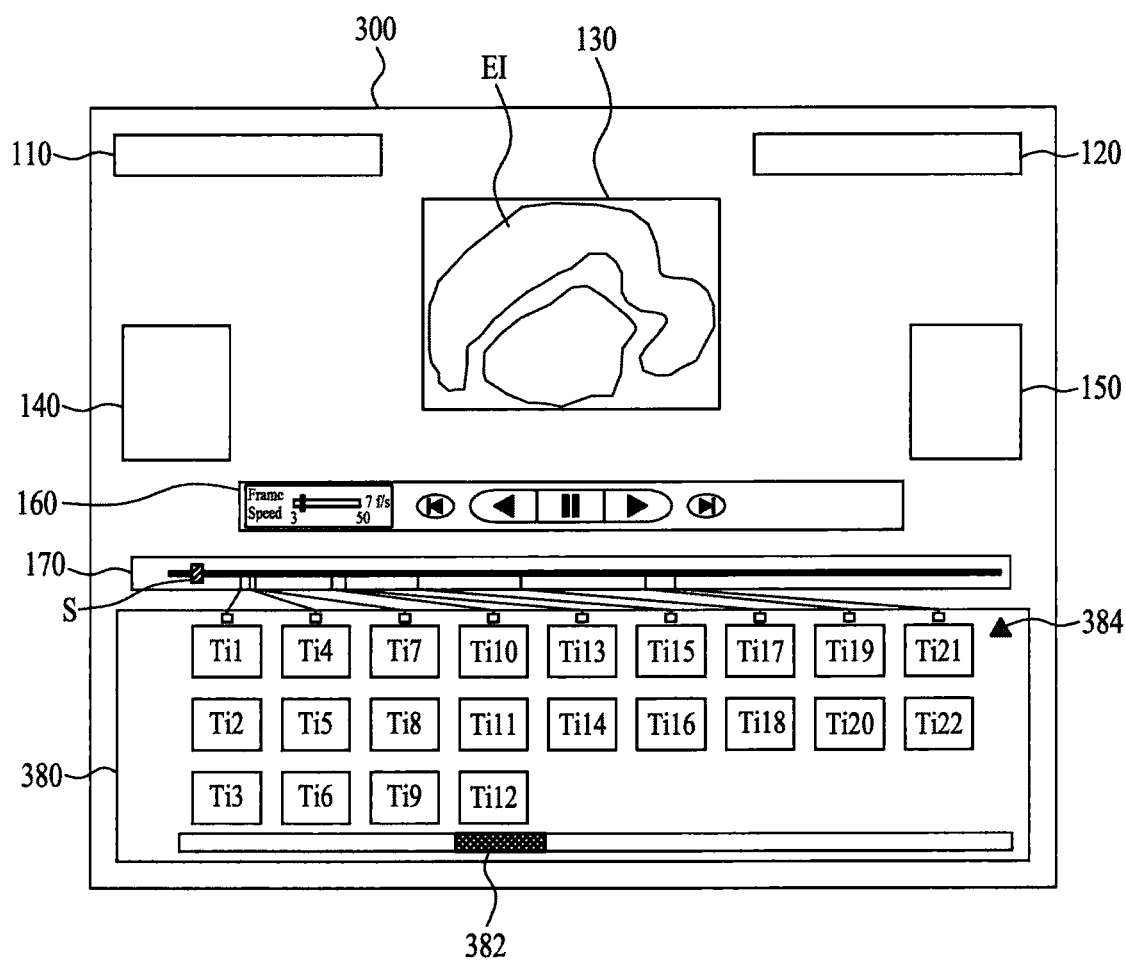
Figure 11C:
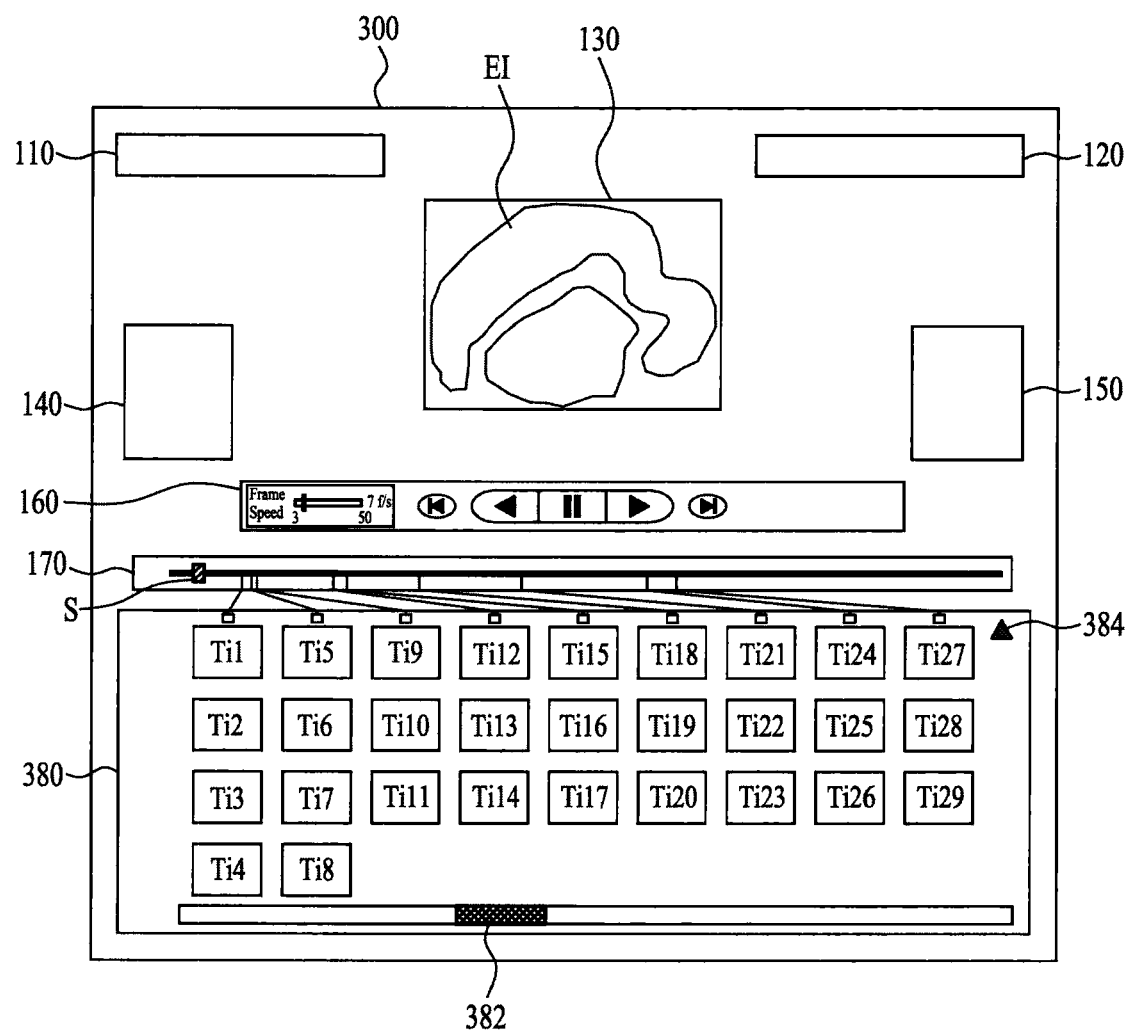

According to another embodiment of the present invention, as shown in FIG. 11A, the enlarged sub-display area may be provided with the capture images (Ti1 to Tin) arranged in 'N×M' matrix configuration according to the number of capture images (Ti1 to Tin), wherein the capture images (Ti1 to Tin) are sequentially arranged along the column direction according to the recording time. In the first row, there are the capture images (Ti1, Ti3, Ti5, Ti7, . . . ) having the earliest recording time among the capture images provided in each column. For example, the capture images (Ti1 to Tin) may be arranged in '2×9' matrix configuration. Selectively, the capture images (Ti1 to Tin) may be arranged in '3×9' matrix configuration as shown in FIG. 11B, or may be arranged in '4×9' matrix configuration as shown in FIG. 11C.

Figure 12:
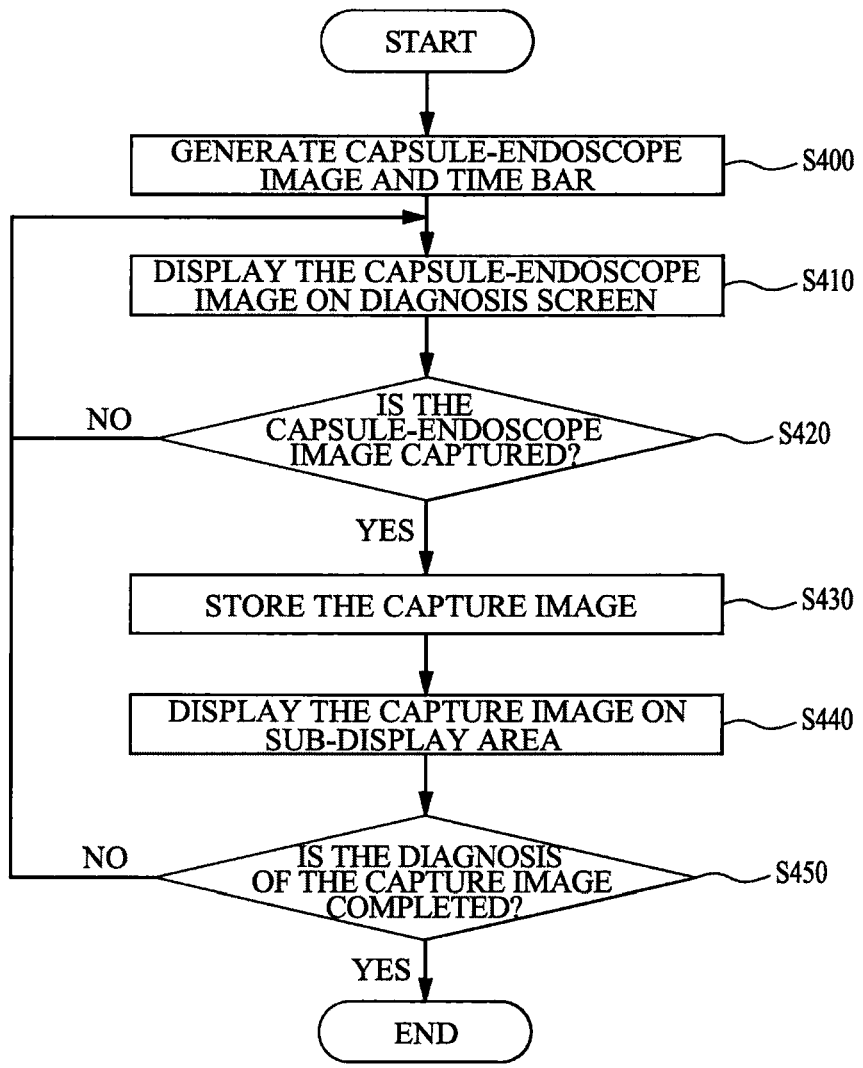
FIG. 12 is a flowchart illustrating a method of displaying an image taken by a capsule endoscope according to the fourth embodiment of the present invention.

FIG. 12 is a flowchart illustrating a method of displaying an image taken by a capsule endoscope according to the fourth embodiment of the present invention.

A method of displaying an image taken by a capsule endoscope according to the fourth embodiment of the present invention will be explained with reference to FIG. 12.

By swallowing a capsule endoscope (not shown), the capsule endoscope is inserted into a subject to be examined, i.e., living body. Then, an image taken by the capsule endoscope (hereinafter, referred to as 'capsule-endoscope image') is generated through the use of image stream data transmitted from the capsule endoscope inserted into the inside of the subject, and a time bar corresponding to the entire capsule-endoscope image is generated in step S400. In this case, the image stream data may be stored in and provided from a storing device (not shown) of a workstation (not shown) through a receiving device which receives the image stream data transmitted from the capsule endoscope, or may be directly provided from the receiving device in real-time.

As shown in FIG. 8, the generated image (E1) is displayed on a diagnosis screen 300 of a display device in step S410.

It is checked whether or not the capsule-endoscope image (E1) displayed on a main-display area 130 is captured by the observer in step S420.

If the capsule-endoscope image (E1) displayed on the main-display area 130 is captured by the observer in step S420 (that is, 'yes' in step S420), the capsule-endoscope image (E1) displayed on the main-display area 130 is captured and is then stored as the capture image (Ti) in step S430.

If the capsule-endoscope image (E1) displayed on the main-display area 130 is not captured by the observer in step S420 (that is, 'no' in step S420), the next capsule-endoscope image (E1) is displayed on the main-display area 130 by the aforementioned step S410.

The stored capture images (Ti) are sequentially displayed on a sub-display area 380 in step S440.

Then, it is checked whether or not the diagnosis of the capsule-endoscope image (E1) is completed by the observer in step S450.

If the diagnosis is completed in step S450, it is determined that the observer completes the diagnosis of the capsule-endoscope image (E1).

If the diagnosis is not completed in step S450, the aforementioned steps S410 to S440 are repetitively performed until completing the diagnosis.

Figure 13:
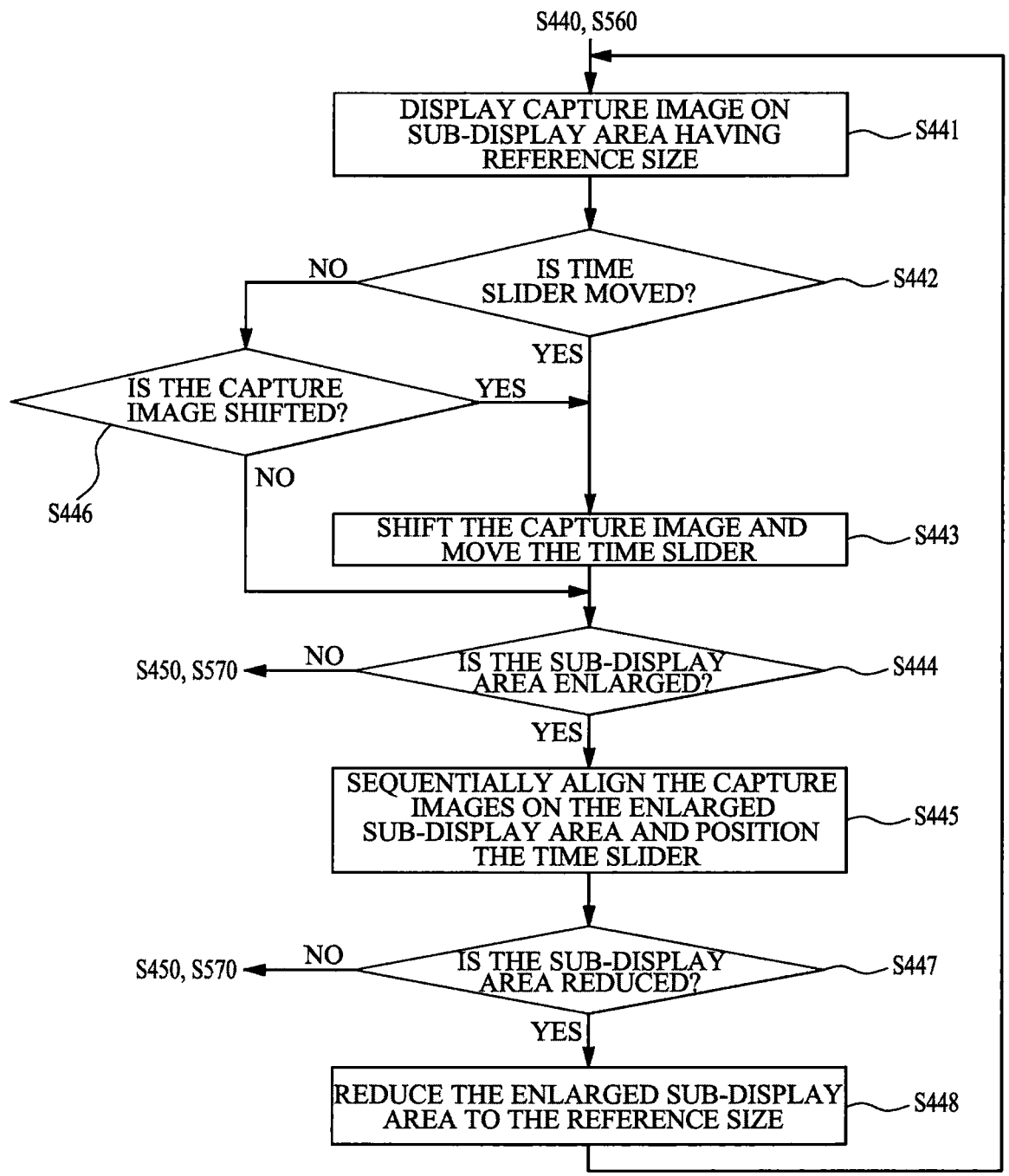
FIG. 13 is a flowchart illustrating a method of displaying a capture image on a sub-display area of FIG. 12.

FIG. 13 is a flowchart illustrating a detailed method of displaying the capture image on the sub-display area of FIG. 12.

A detailed method of displaying the capture image on the sub-display area will be explained with reference to FIG. 13 in conjunction with FIGS. 8 and 12.

First, the stored capture images (Ti) are sequentially displayed on the sub-display area 380 in step S441.

Then, it is checked whether or not the time slider (S) is moved by the observer in step S442.

If the time slider (S) is moved by the observer in step S442 (that is, 'yes' in step S442), the time corresponding to the position of the moved time slider (S) is detected, and the capture image (Ti) is shifted according to the detected time of the time slider (S), whereby other capture images (Ti) being adjacent to the detected time of the time slider (S) are aligned and displayed on the sub-display area 380 in step S443.

It is checked whether or not the observer enlarges the sub-display area 380 by operating an enlarging/reducing button 384 in step S444.

If the observer enlarges the sub-display area 380 in step S444 (that is, 'yes' in step S444), as shown in any one of FIGS. 10 to 11C, the sub-display area 380 is enlarged; the size of the enlarged sub-display area 380 is measured; the total number of the stored capture images (Ti) is measure; the capture images (Ti) are displayed in the matrix configuration through the sequential alignment on the basis of the size of the enlarged sub-display area 380; and the time slider (S) is moved to be positioned at the predetermined portion of the time bar corresponding to the recording time of the reference capture image (Ti) among the aligned capture images (Ti) in step S445.

If the time slider (S) is not moved by the observer in step S442 (that is, 'no' in step S442), it is checked whether or not the observer shifts the capture image (Ti) by moving a scroll bar 382 in step S446.

If the observer moves the scroll bar 382 (that is, 'yes' in step S446), the recording time of the reference capture image (Ti) displayed at a reference point of the sub-display area 380 is detected, and the time slider (S) is moved according to the detected recording time of the capture image (Ti) in step S443.

In the meantime, if the observer does not move the scroll bar 382 (that is, 'no' in step S446), the aforementioned step S444 is performed.

If the sub-display area 380 is not enlarged by the observer in step S444 (that is, 'no' in step S444), the aforementioned step S450 of FIG. 12 is performed.

It is checked whether or not the enlarged sub-display area 380 is reduced by the observer through the operation of the enlarging/reducing button 384 in step S447.

If the observer reduces the enlarged sub-display area 380 in step S447 (that is, 'yes' in step S447), as shown in FIG. 8, the enlarged sub-display area 380 is reduced in step S448, and then the aforementioned steps S441 to S447 are performed in sequence.

If the observer does not reduce the enlarged sub-display area 380 in step S447 (that is, 'no' in step S447), the aforementioned step S450 of FIG. 12 is performed.

In the method of displaying the capsule-endoscope image according to the fourth embodiment of the present invention, the movement of the capture image (Ti) is linked with the movement of the time slider (S) according to the observer's operation, and the increased number of capture images (Ti) is displayed on the sub-display area 380 enlarged by the observer's operation, to thereby improve diagnosis efficiency.

Figure 14:
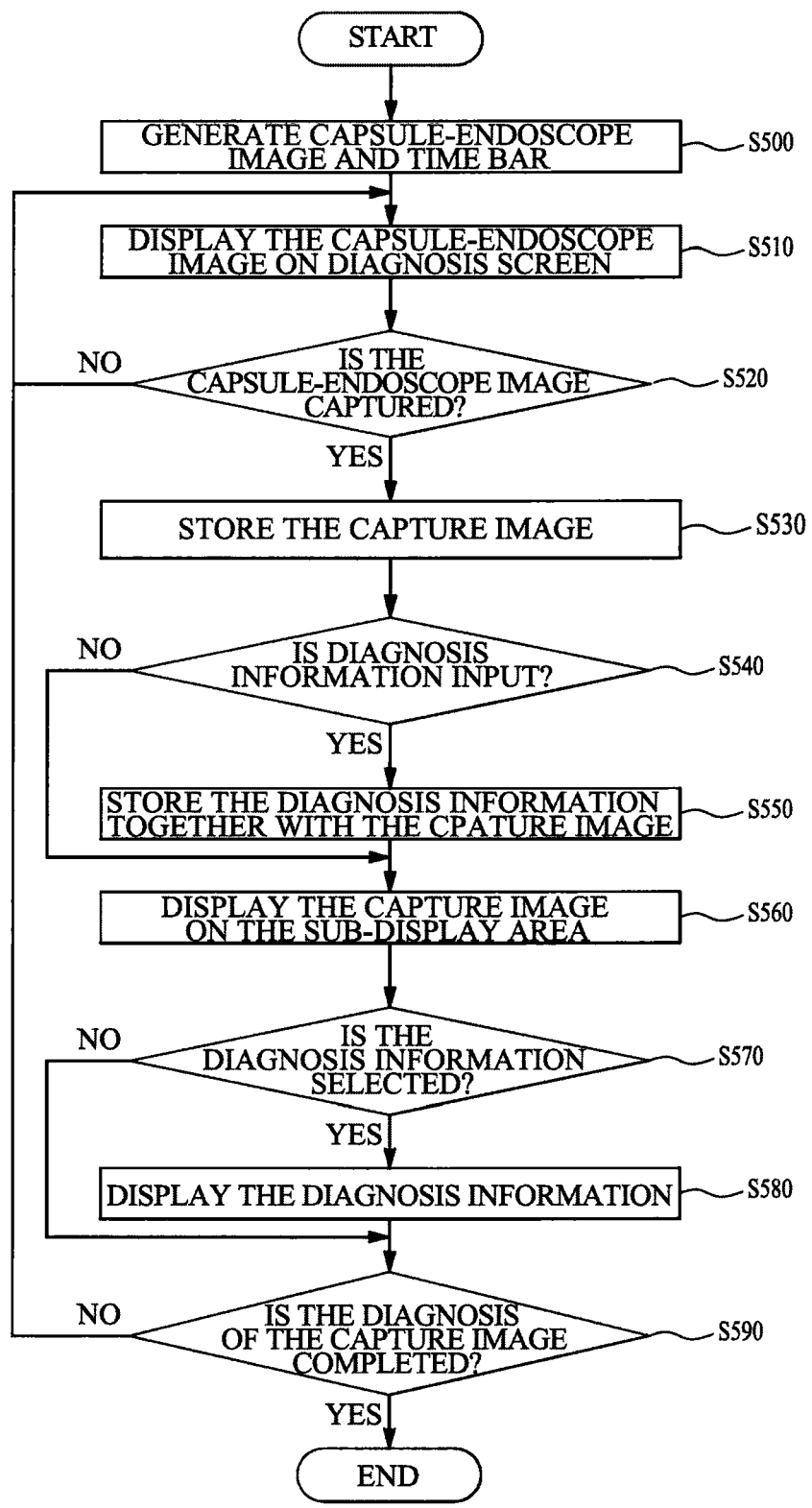
FIG. 14 is a flowchart illustrating a method of displaying an image taken by a capsule endoscope according to the fifth embodiment of the present invention.

FIG. 14 is a flowchart illustrating a method of displaying an image taken by a capsule endoscope according to the fifth embodiment of the present invention.

A method of displaying an image taken by a capsule endoscope according to the fifth embodiment of the present invention will be explained with reference to FIG. 14.

By swallowing a capsule endoscope (not shown), the capsule endoscope is inserted into a subject to be examined, i.e., living body. Then, an image taken by the capsule endoscope (hereinafter, referred to as 'capsule-endoscope image') is generated through the use of image stream data transmitted from the capsule endoscope inserted into the inside of the subject, and a time bar corresponding to the entire capsule-endoscope image is generated in step S500. In this case, the image stream data may be stored in and provided from a storing device (not shown) of a workstation (not shown) through a receiving device which receives the image stream data transmitted from the capsule endoscope, or may be directly provided from the receiving device in real-time.

Figure 15:
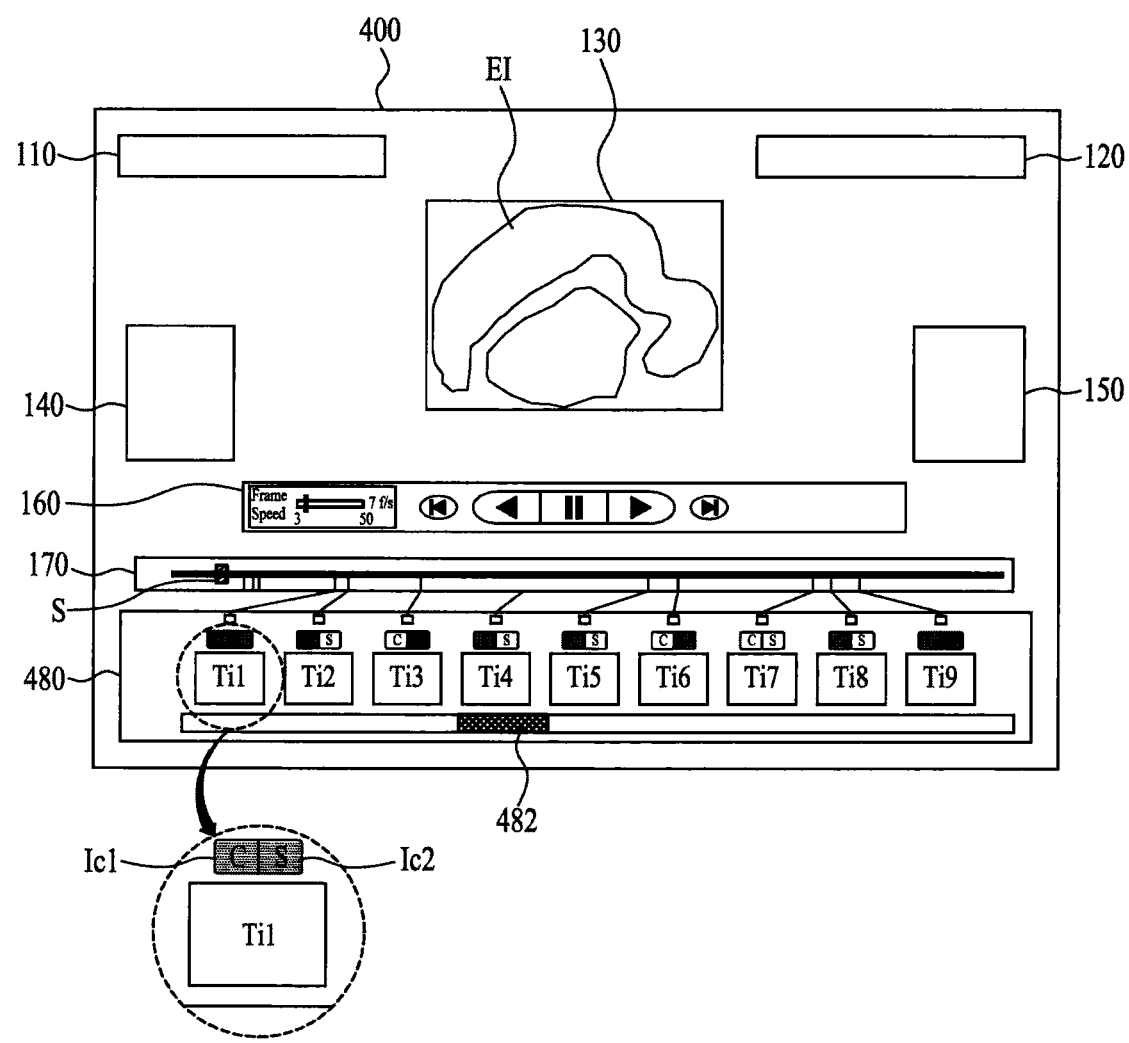
FIG. 15 illustrates a diagnosis screen in the image displaying method according to the fifth embodiment of the present invention.

As shown in FIG. 15, the generated image (E1) is displayed on a diagnosis screen 400 of a display device (not shown) in step S410.

At this time, the diagnosis screen 400 includes a program tool menu 110, a view/mode menu 120, a main-display area 130, a capsule-endoscope position display area 140, a comparative image display area 150, a play menu 160, a time bar display area 170, and a sub-display area 480. Except the sub-display area 480, the diagnosis screen 400 according to the fifth embodiment of the present invention is identical in structure to the diagnosis screen 200 according to the second embodiment of the present invention, whereby the detailed explanation for the same structures will be omitted.

A capture image (Ti) captured by the observer is displayed on the sub-display area 480 in such a way that the capture image (Ti) is linked with the time bar display area 170.

Also, the sub-display area 480 includes a scroll bar 482 for shifting the capture images (Ti) leftward or rightward; and first and second diagnosis information icons (Ic1, Ic2) displayed at the upper side of each capture image (Ti).

In the same manner as the second embodiment of the present invention, the scroll bar 482 is moved by the observer's operation. The capture images (Ti) may be shifted while being linked with the movement of the scroll bar 482, or may be shifted while being linked with the movement of the time slider (S).

The first diagnosis information icon (Ic1) is a menu to provide text information about each capture image (Ti) input by the observer, for example, diseases, bleeding, and the kind of intestines.

The second diagnosis information icon (Ic2) is a menu to provide sound information about each capture image (Ti).

In FIG. 14, it is checked whether or not the capsule-endoscope image (E1) displayed on the main-display area 130 is captured by the observer in step S520.

If the capsule-endoscope image (E1) displayed on the main-display area 130 is captured by the observer in step S520 (that is, 'yes' in step S520), the capsule-endoscope image (E1) displayed on the main-display area 130 is captured, and is stored as the capture image (Ti) in step S530.

If the capsule-endoscope image (E1) displayed on the main-display area 130 is not captured by the observer in step S520 (that is, 'no' in step S520), the next capsule-endoscope image (E1) is displayed on the main-display area 130 through the aforementioned step S510.

It is checked whether or not the observer inputs diagnosis information corresponding to a diagnosis result of the capture image in step S540.

If the observer inputs the diagnosis information about the capture image (that is, 'yes' in step S540), the input diagnosis information is stored in the corresponding capture image in step S550. At this time, the diagnosis information about the capture image may be text information (C) or sound information (S) about diseases, bleeding, and the kind of intestines.

The first and second diagnosis information icons (Ic1, Ic2) corresponding to the diagnosis result of the stored capture image (Ti) are sequentially displayed on the sub-display area 480 in step S560. At this time, the first and second diagnosis information icons (Ic1, Ic2) are displayed as the active state to inform the observer of the existence of the text information (C) and sound information (S) about the corresponding capture image (Ti), as shown in FIG. 15.

If the observer does not input the diagnosis information about the capture image (that is, 'no' in step S540), the capture image (Ti) stored by the aforementioned step S530 is displayed on the sub-display area 480 through the aforementioned step S560. At this time, the first and second diagnosis information icons (Ic1, Ic2) are displayed as the inactive state to inform the observer of the inexistency of the text information (C) and sound information (S) about the corresponding capture image (Ti), as shown in FIG. 15.

Then, it is checked whether or not the observer selects the diagnosis information corresponding to the capture image (Ti) displayed on the sub-display area 480 in step S570.

If the observer selects the diagnosis information corresponding to the capture image (Ti) displayed on the sub-display area 480 in step S570 (that is, 'yes' in step S570), the selected diagnosis information is displayed on the diagnosis screen 400 in step S580.

Figure 16A:
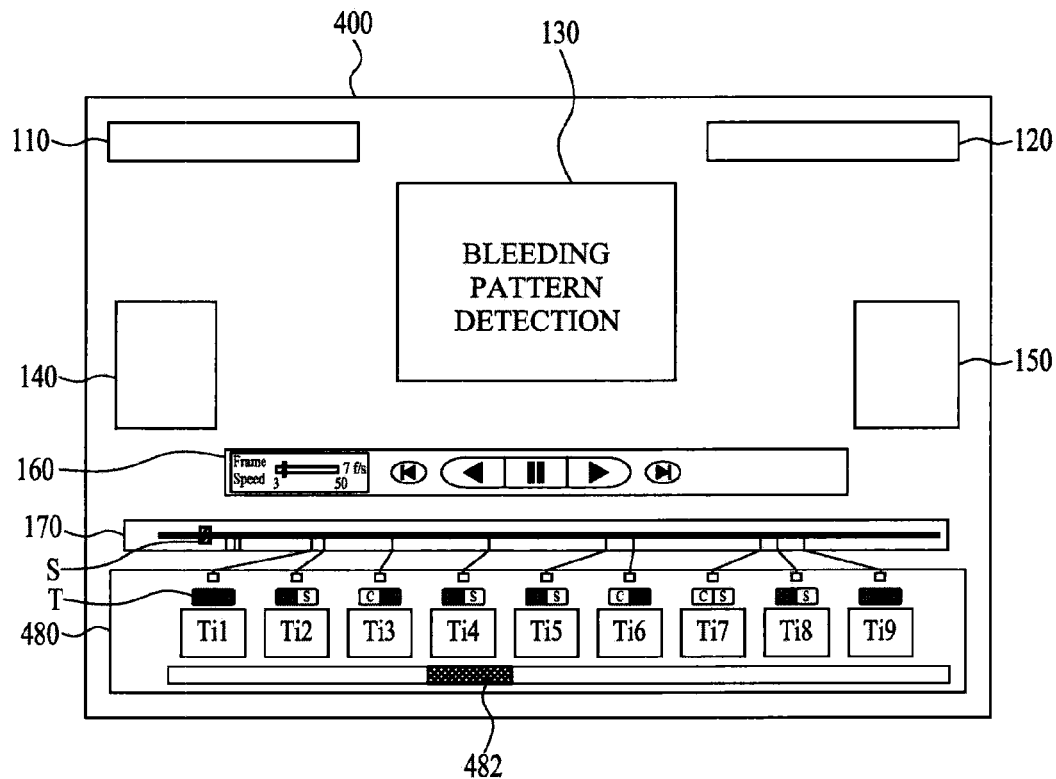
FIGS. 16A to 16C illustrate a method of displaying diagnosis information of FIG. 14.

According to one embodiment of the present invention, as shown in FIG. 16A, if the observer selects the activated first diagnosis information icon (Ic1) of the corresponding capture image (Ti1) through the use of mouse or keyboard, the text information (C) of the corresponding capture image (Ti1) may be displayed on the main-display area 130.

Figure 16B:
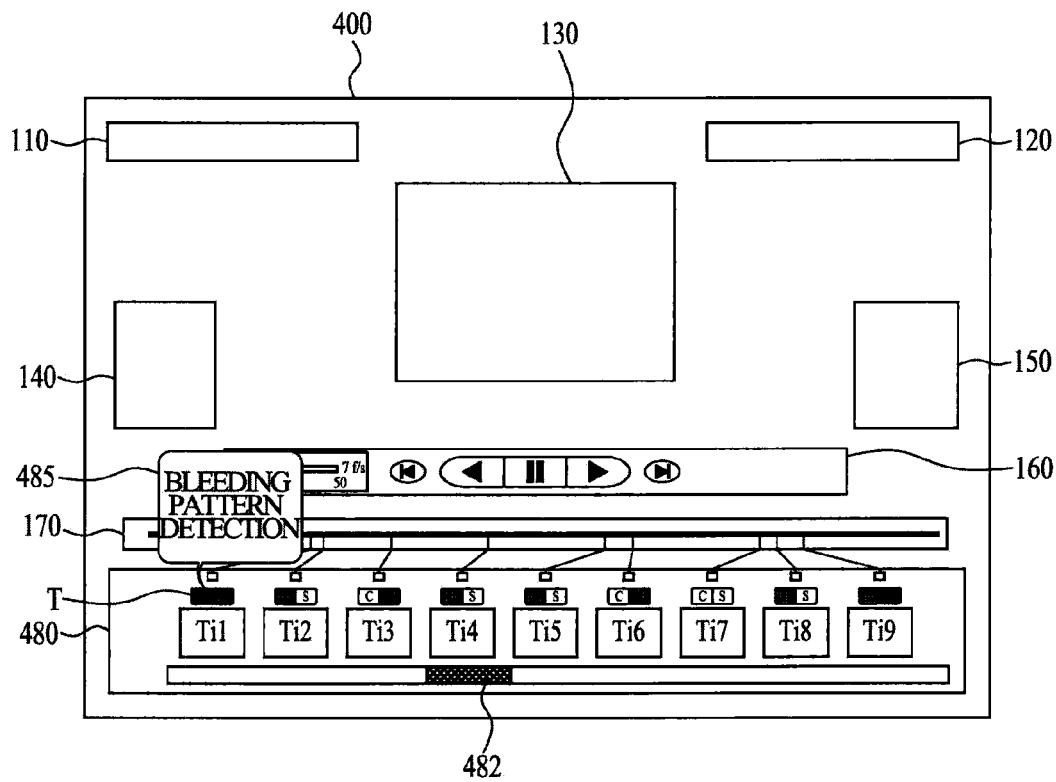

According to another embodiment of the present invention, as shown in FIG. 16B, if the observer selects the activated first diagnosis information icon (Ic1) of the corresponding capture image (Ti1) through the use of mouse or keyboard, the text information (C) of the corresponding capture image (Ti1) may be displayed on an additional popup window 485.

Figure 16C:
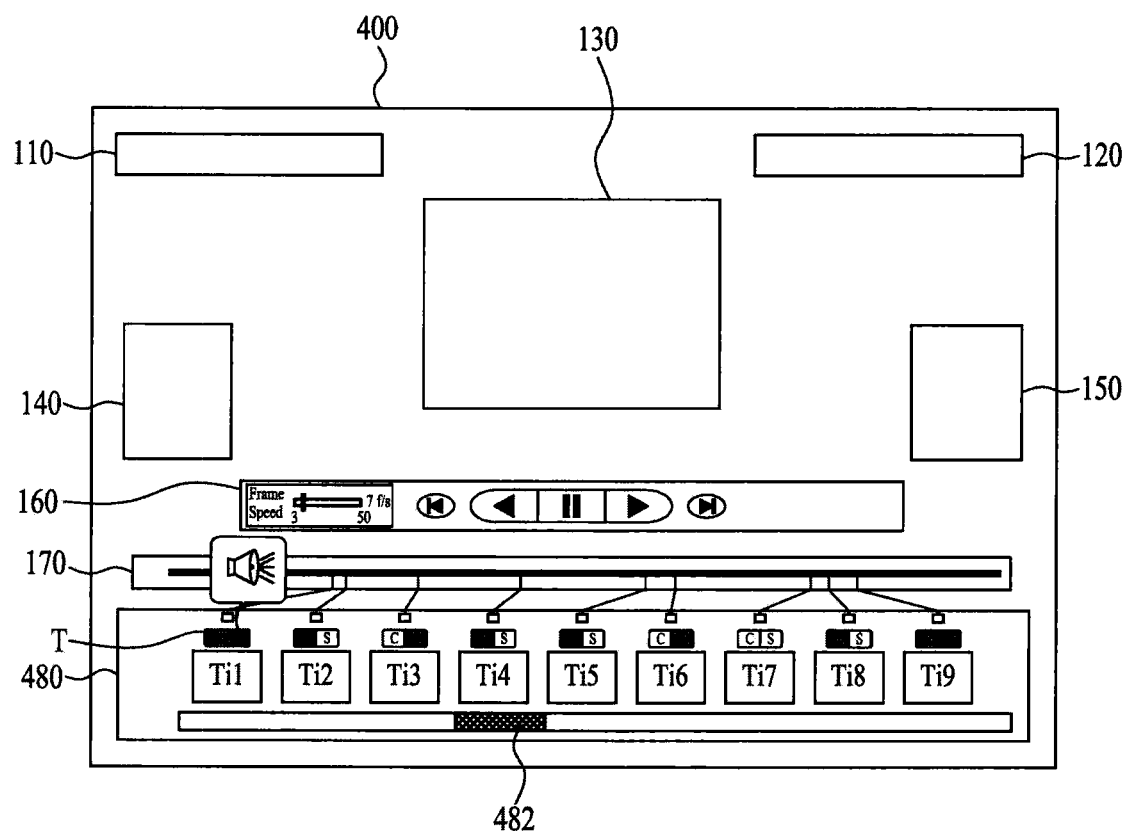

According to another embodiment of the present invention, as shown in FIG. 16C, if the observer selects the activated second diagnosis information icon (Ic2) of the corresponding capture image (Ti1) through the use of mouse or keyboard, the sound information (S) of the corresponding capture image (Ti1) may be displayed.

Thereafter, it is checked whether or not the diagnosis of the capsule-endoscope image (E1) is completed by the observer in step S590.

If the diagnosis is completed in step S590, it is determined that the observer completes the diagnosis of the capsule-endoscope image (E1).

If the diagnosis is not completed in step S590, the aforementioned steps S510 to S580 are repetitively performed until completing the diagnosis.

The method of displaying the capsule-endoscope image according to the fifth embodiment of the present invention can inform the observer of the text information (C) or sound information (S) about the capture image (Ti), whereby the observer can reduce a time period consumed in writing the report and examining the diagnosis.

In the method according to the fifth embodiment of the present invention, the movement of the capture image (Ti) is linked with the movement of the time slider (S) in the aforementioned step S560 according to the observer's operation through the aforementioned steps S441 to S448 shown in FIG. 13, and more capture images (Ti) can be displayed on the sub-display area 480 enlarged by the observer's operation.

The aforementioned first to fifth embodiments of the present invention disclose that the respective capture images are displayed on the sub-display area by the observer's operation. However, modified embodiments of the present invention may disclose that a plurality of capture images are grouped into capture image bags and the capture image bags are displayed on a sub-display area. Hereinafter, a method of displaying an image taken by a capsule endoscope, which is capable of displaying the capture image bags on the sub-display area, will be explained as follows.

Figure 17:
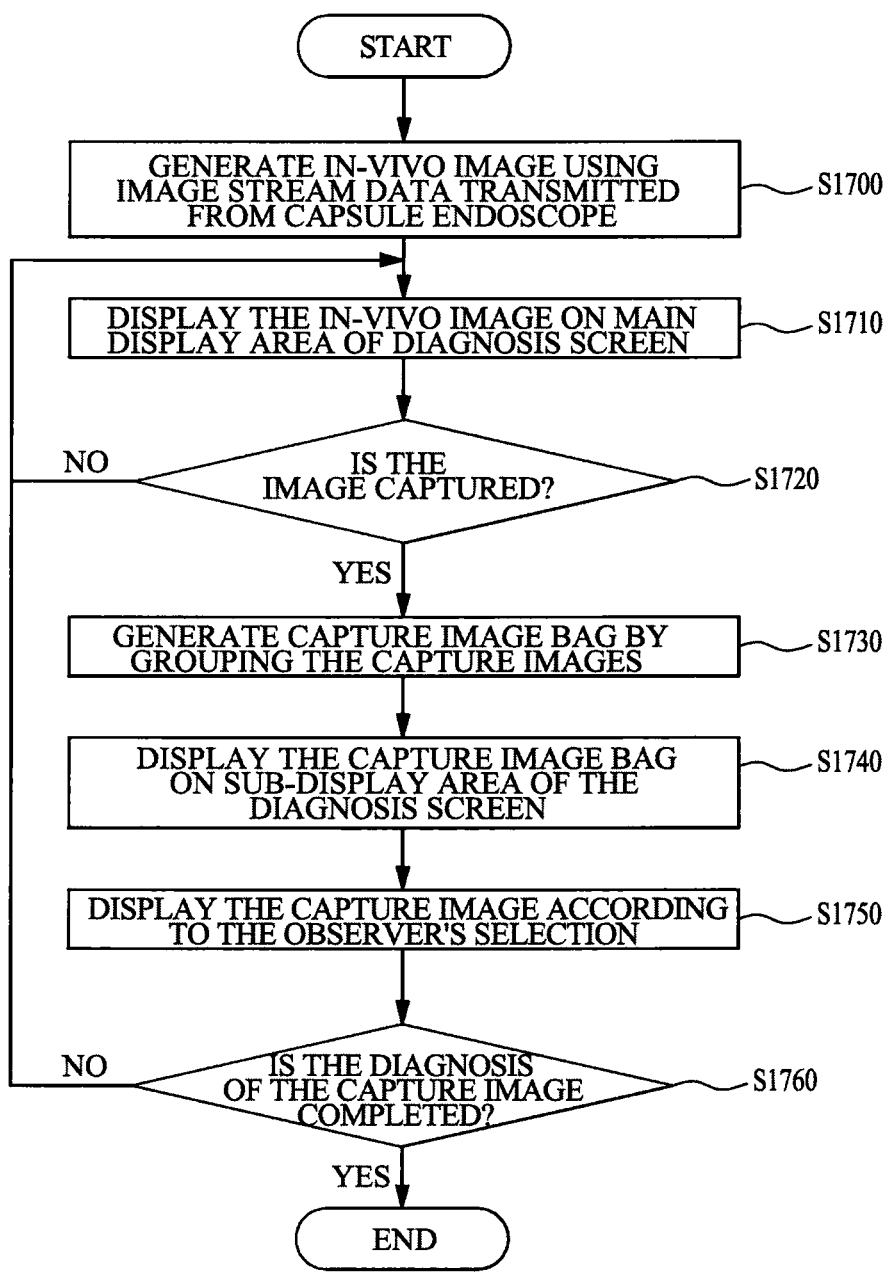
FIG. 17 is a flowchart illustrating a method of displaying a capture image bag on a sub-display area according to the embodiment of the present invention.

FIG. 17 is a flowchart illustrating the method of displaying the image taken by the capsule endoscope, which is capable of displaying the capture image bags on the sub-display area.

By swallowing a capsule endoscope (not shown), the capsule endoscope is inserted into a subject to be examined, i.e., living body. Then, an in-vivo image is generated through the use of image stream data transmitted from the capsule endoscope inserted into the inside of the subject in step S1700. In this case, the image stream data may be stored in and provided from a storing device (not shown) of a workstation (not shown) through a receiving device which receives the image stream data transmitted from the capsule endoscope, or may be directly provided from the receiving device in real-time.

Figure 18:
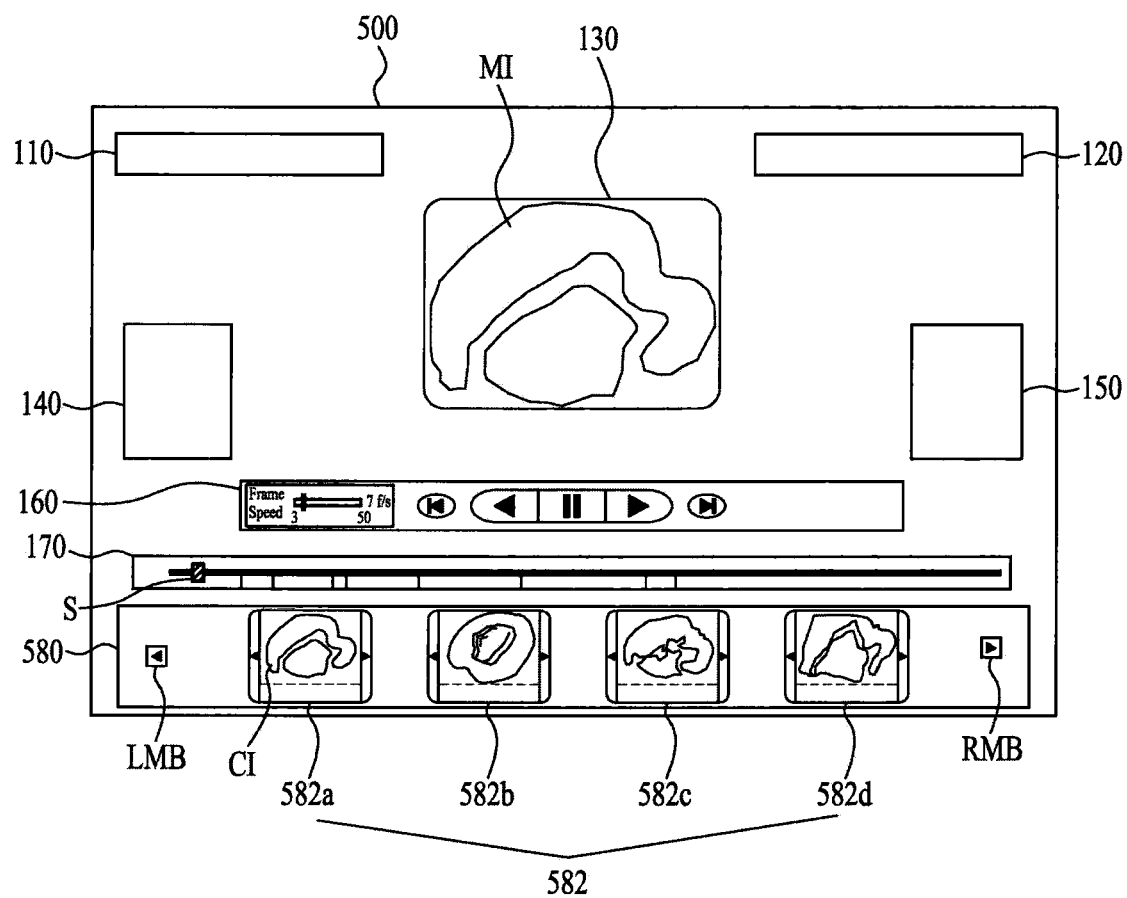
FIG. 18 illustrates a diagnosis screen in the displaying method of the capture image bag according to the embodiment of the present invention.

The generated in-vivo image (MI) is displayed on a main-display area 130 of a diagnosis screen 500 in step S1710. As shown in FIG. 18, the diagnosis screen 500 includes a program tool menu 110, a view/mode menu 120, the main-display area 130, a capsule-endoscope position display area 140, a comparative image display area 150, a play menu 160, a time bar display area 170, and a sub-display area 580. Except the sub-display area 580, the diagnosis screen 500 is identical in structure to the diagnosis screen 100 according to the first embodiment of the present invention, whereby the detailed explanation for the same structures will be omitted.

On the sub-display area 580, the plurality of capture image bags 582, formed by grouping the plurality of capture images (CI) obtained from the in-vivo image (MI) displayed on the main-display area 130, are displayed.

As shown in FIG. 18, the sub-display area 580 may include first and second moving buttons (LMB, RMB).

The first moving button (LMB) is provided at one side of the sub-display area 580. Whenever the observer clicks on the first moving button (LMB), the capture image bags 582 displayed on the sub-display area 580 are sequentially shifted rightward, so that the unseen capture image bag 582 prior to the leftmost capture image bag 582 is displayed on the sub-display area 580.

The second moving button (RMB) is provided at the other side of the sub-display area 580. Whenever the observer clicks on the second moving button (RMB), the capture image bags 582 displayed on the sub-display area 580 are sequentially shifted leftward, so that the unseen capture image bag 582 prior to the rightmost capture image bag 582 is displayed on the sub-display area 580.

Referring once again to FIG. 17, it is checked whether or not the in-vivo image (MI) displayed on the main-display area 130 is captured in step S1720. At this time, the in-vivo image (MI) can be captured by the observer's selection or every time period. If the in-vivo image (MI) displayed on the main-display area 130 is captured in step S1720 (that is, 'yes' in step S1720), the in-vivo image (MI) displayed on the main-display area 130 is captured, and the capture image (CI) is grouped, thereby generating the capture image bag 582 in step S1730. At this time, the capture image (CI) may be grouped into the capture image bag 582 selected by the observer, or may be grouped into the capture image bag 582 every recording time.

Figure 19A:
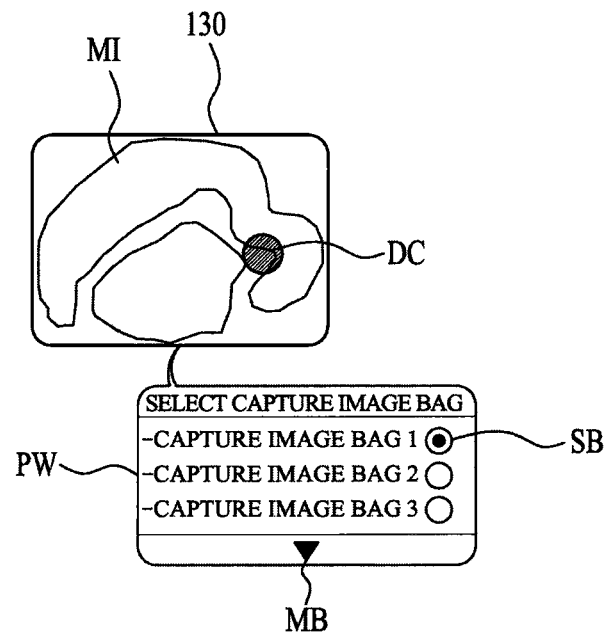
FIGS. 19A to 19C illustrate a method of capturing an in-vivo image according to an observer's selection.

In the method of generating the capture image bag 582 according to the first embodiment of the present invention, as shown in FIG. 19A, the observer can capture the in-vivo image (MI) by double clicking on the in-vivo image (MI) displayed on the main-display area 130 through the use of mouse. That is, if the observer double clicks on the in-vivo image (MI), a popup window (PW) is displayed to enable the observer to select the desired capture image bag 582. Accordingly, as the observer selects the desired capture image bag 582 from the popup window (PW), the capture image is stored in and grouped into the desired capture image bag 582. For this, the popup window (PW) includes a message such as "Select the capture image bag", and the popup window (PW) includes a selection button (SB) for selecting the capture image bag 582, and a down button (MB) for the shift to the observer's desired capture image bag 582.

Figure 19B:
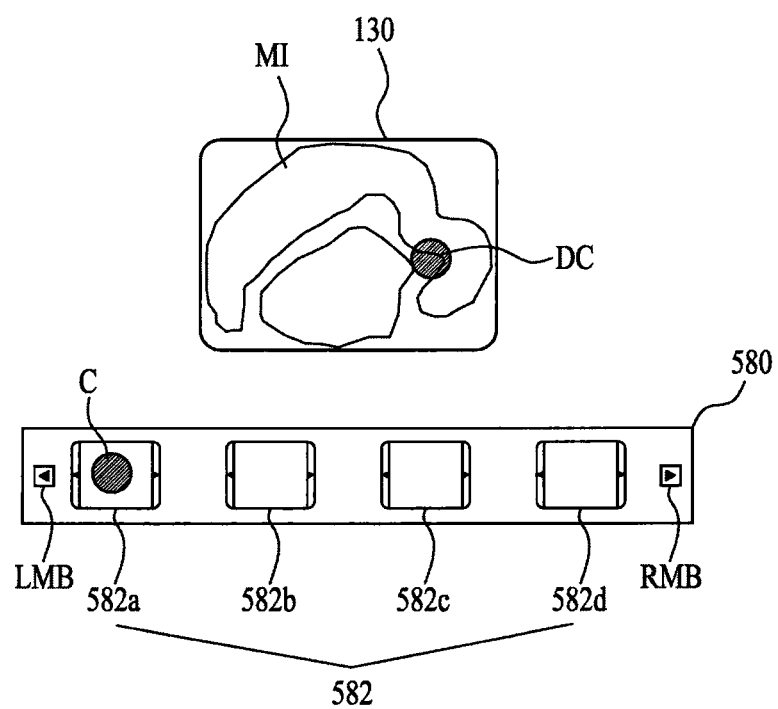

In the method of generating the capture image bag 582 according to the second embodiment of the present invention, as shown in FIG. 19B, if the observer double clicks on the in-vivo image (MI), the sub-display area 580 with the plurality of capture image bags 582 is enlarged on the diagnosis screen 500 so that the observer is capable of selecting the desired capture image bag 582 from the enlarged sub-display area 580. As the observer selects the desired capture image bag 582a from the plurality of capture image bags 582a, 582b, 582c, and 582d displayed on the enlarged sub-display area 580, the capture image is stored in and grouped into the desired capture image bag 582.

Figure 19C:
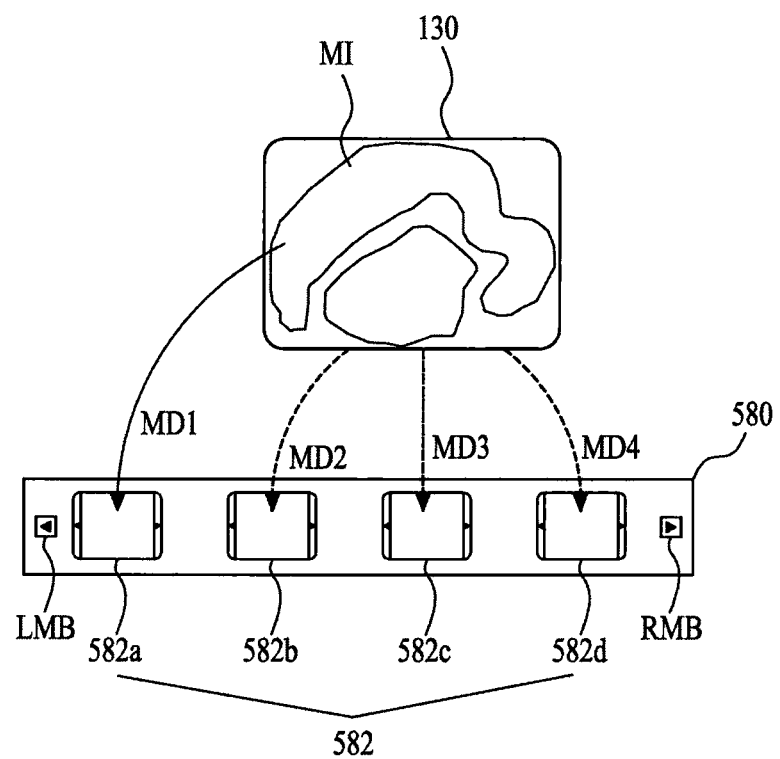

In the method of generating the capture image bag 582 according to the third embodiment of the present invention, as shown in FIG. 19C, the observer can capture the in-vivo image (MI) displayed on the main-display area 130 through the use of drag and drop operation (MD1, MD2, MD3, and MD4) of mouse; and store the captured images in the desired capture image bags 582*a*, 582*b*, 582*c*, and 582*d* displayed on the sub-display area 580, whereby the capture images are grouped into the capture image bags.

In the aforementioned first to third embodiments of the present invention, the observer can capture the in-vivo image (MI) by each of intestines, bleeding and diseases; and can group the capture images into the desired capture image bags 582*a*, 582*b*, 582*c*, and 582*d*.

Figure 20:
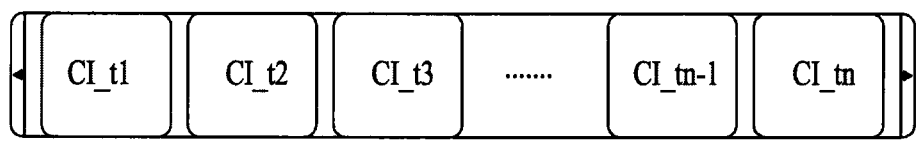
FIG. 20 illustrates a method of capturing an in-vivo image every fixed interval.

In the method of generating the capture image bag 582 according to the fourth embodiment of the present invention, the capture images (CI) may be captured every recording time of fixed interval, and grouped into and stored in the respective capture image bags 582. That is, as shown in FIG. 20, the capture images (CI_t1, CI_t2, CI_t3, CI_t4, . . . , CI_tn) which are obtained by automatically capturing the in-vivo image (MI) displayed on the main-display area 130 every recording time of preset interval (t), may be grouped into the respective capture image bags 582.

Referring once again to FIG. 17, if the in-vivo image (MI) displayed on the main-display area 130 is not captured in the aforementioned step S1720 (that is, 'no' in S1720), the next in-vivo image (MI) is displayed on the main-display area 130 through the aforementioned step S1710.

Then, the generated capture image bags 582 are displayed at fixed intervals on the sub-display area 580 of the diagnosis screen 500 in step S1740.

Figure 21:
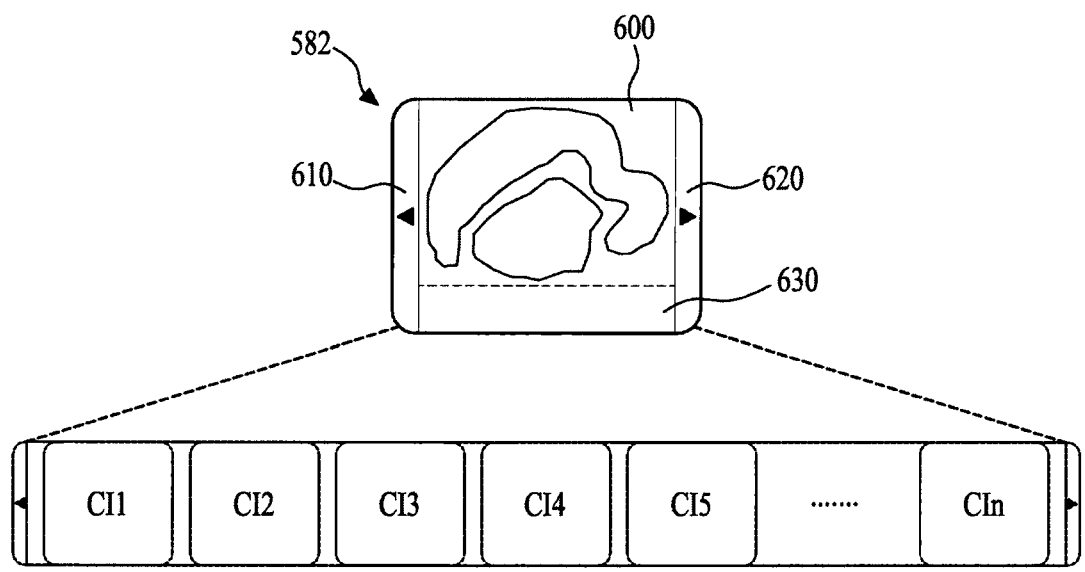
FIG. 21 illustrates the capture image bag according to the embodiment of the present invention.

At this time, the capture image bag 582 displayed on the sub-display area 580 may include a capture image display area 600, a first button area 610, a second button area 620, and a group information display area 630, as shown in FIG. 21.

The capture image display area 600 is provided at the center of each capture image bag 582. Among the capture images (CI1 to CIn) grouped into the respective capture image bags 582, any one representative capture image (CI) is displayed on the capture image display area 600. At this time, the capture image (CI) may be displayed on the capture image display area 600 in such a way that the capture image (CI) may have the same size as the in-vivo image (MI) displayed on the main-display area 130, or may be reduced by a predetermined ratio.

The first button area 610 is provided at one side of the capture image display area 600, wherein the first button area 610 includes a first button for displaying other capture image taken prior to the recording time of the representative capture image on the capture image display area 600.

The second button area 620 is provided at the other side of the capture image display area 600, wherein the second button area 620 includes a second button for displaying other capture images taken after the recording time of the representative capture image on the capture image display area 600.

The group information display area 630 displays at least one of the total number of capture images grouped into each capture image bag 582, and the range of recording time of the grouped capture images (the earliest recording time and the latest recording time).

The respective capture image bags 582 may display the grouped capture images (CI1 to CIn) according to the observer's selection.

Referring once again to FIG. 17, according to the observer's selection for at least one of the capture image display area 600, the first button area 610, and the second button area 620 in each capture image bag 582, at least one of the capture images (CI) grouped by each capture image bag 582 displayed on the sub-display area 580 is displayed in step S1750.

Figure 22A:
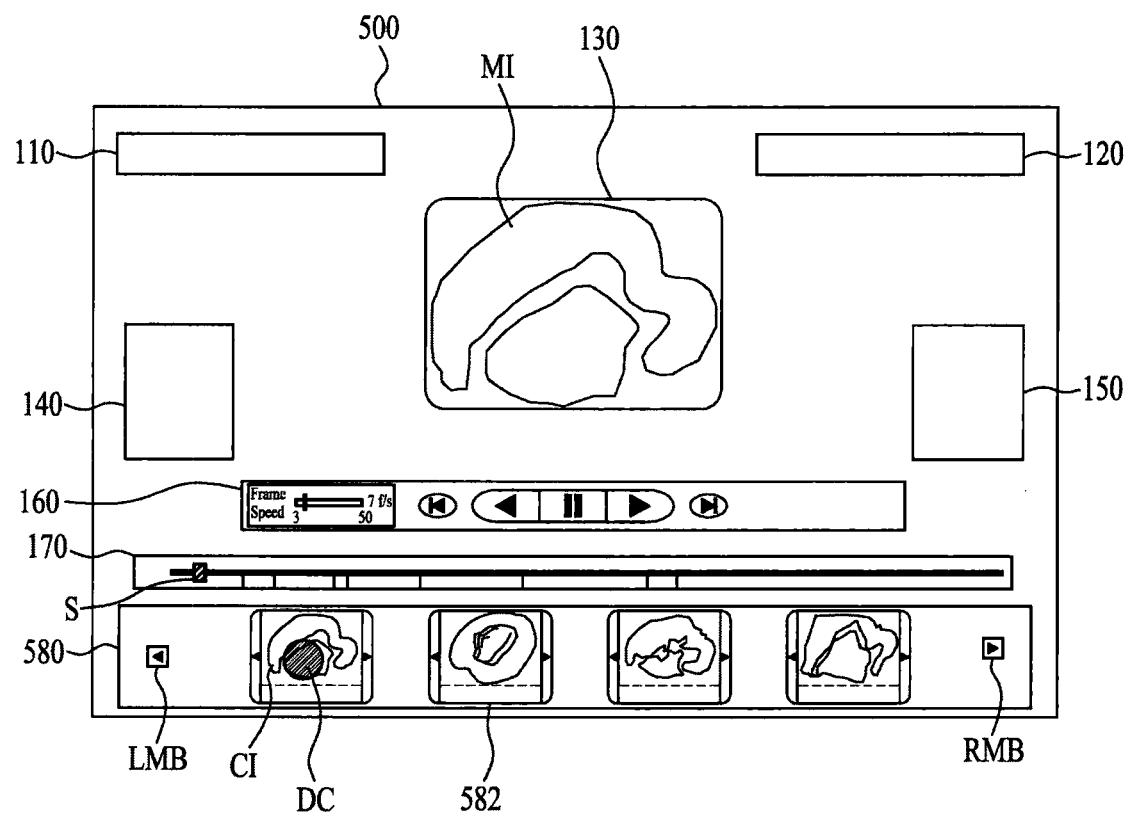
FIGS. 22A and 22B illustrate a method of displaying capture images grouped in a capture image bag according to an observer's selection.
Figure 22B:
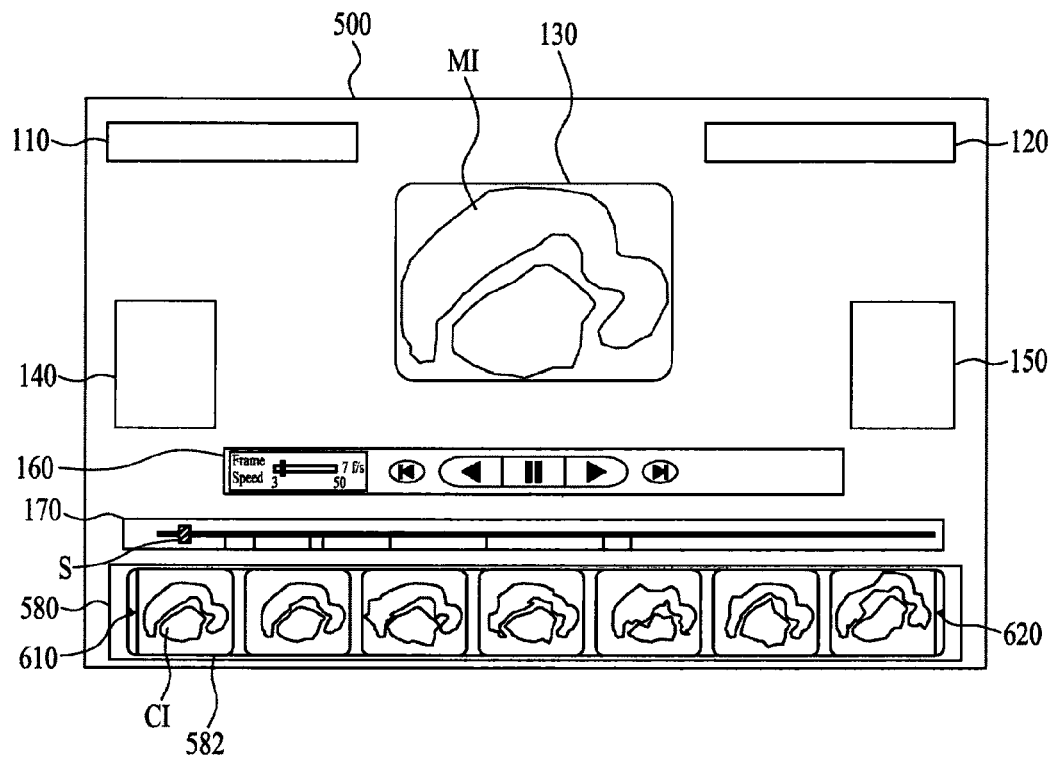

In the method of displaying at least one of the capture images grouped by the capture image bag according to the first embodiment of the present invention, as shown in FIG. 22A, if the observer double clicks on at least any one of the respective capture image display areas 600 in the plurality of capture image bags 582 displayed on the sub-display area 580 through the use of mouse, the capture image display area 600 of the selected capture image bag 582 is enlarged, and the plurality of capture images (CI) grouped into the capture image bag 582 are arranged at fixed intervals on the enlarged capture image display area 600, whereby the observer can observe the plurality of capture images (CI) grouped into the capture image bag 582. In this case, the capture images (CI) displayed on the capture image bag 582 may have the same size as the in-vivo image (MI) displayed on the main-display area 130, or may be reduced by a predetermined ratio.

A button direction displayed on the first button area 610 of the enlarged capture image bag 582 is changed from (◄) to (►), and simultaneously a button direction displayed on the second button area 620 of the enlarged capture image bag 582 is changed from (►) to (◄).

If the observer double clicks on the predetermined capture image (CI) displayed on the enlarged capture image bag 582 of the sub-display area 580 through the use of mouse, or clicks or double clicks on the first or second button area 620 or 620, the capture image display area 600 of the enlarged capture image bag 582 is reduced, and the representative capture image is displayed on the reduced capture image display area 600, whereby the observer can observe the representative capture image among the capture images (CI) grouped in the capture image bag 582. At this time, the representative capture image displayed on the capture image display area 600 is also displayed on the main-display area 130.

If the observer clicks on the first or second button area 610 or 620 of the enlarged capture image bag 582, the observer can observe the capture images (CI) grouped into the capture image bag 582 under such circumstance that the capture images (CI) grouped into the capture image bag 582 are sequentially played while being shifted leftward or rightward. At this time, the capture image shifted by the observer is displayed on the main-display area 130.

Figure 23A:
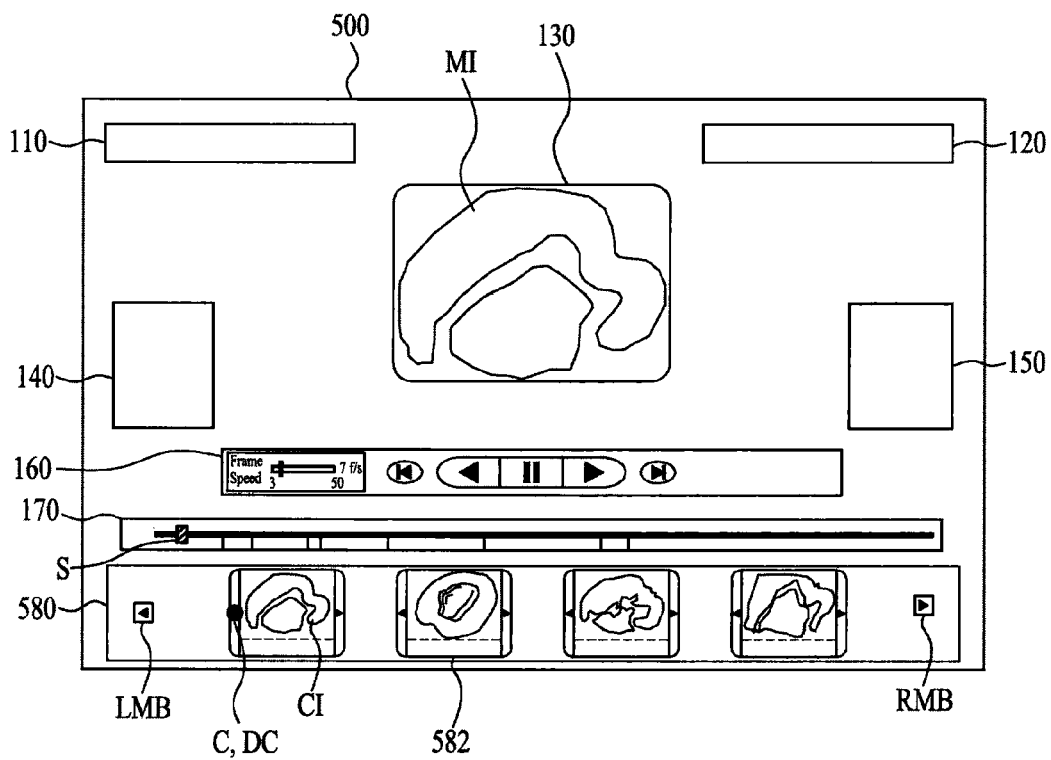
FIGS. 23A to 23C illustrate another method of displaying capture images grouped in a capture image bag according to an observer's selection.
Figure 23B:
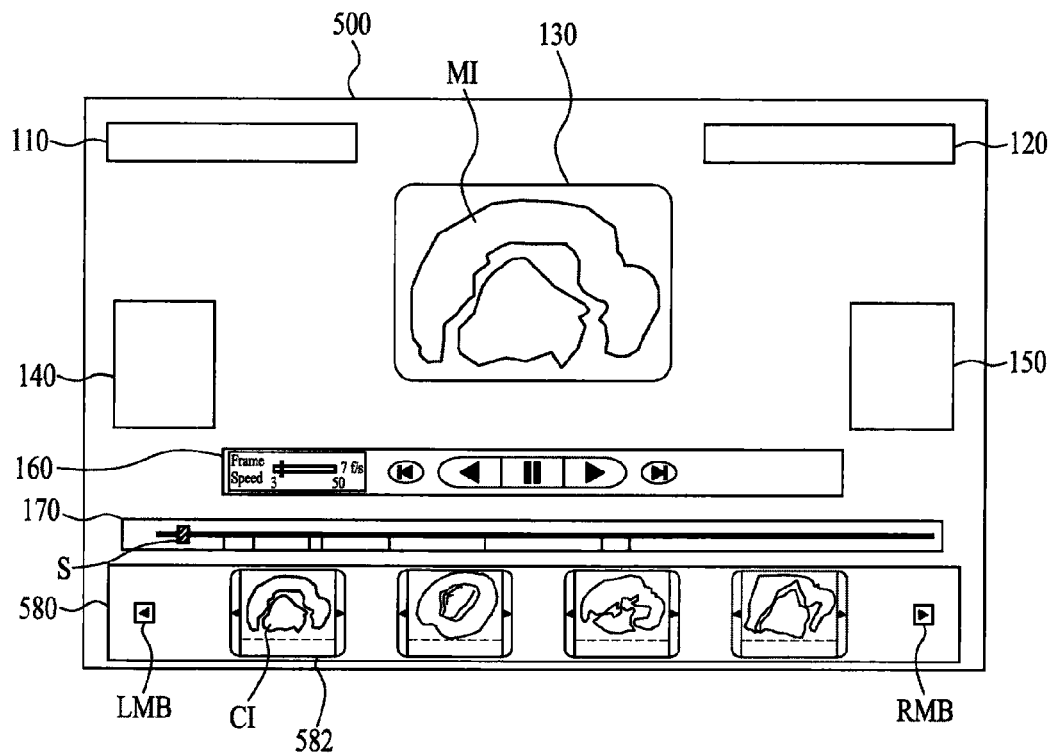

In the method of displaying at least one of the capture images grouped into the capture image bag according to the second embodiment of the present invention, as shown in FIG. 23A, if the observer clicks (which will be referred to as 'first selection', C) on at least any one of the first button areas 610 in the plurality of capture image bags 582 displayed on the sub-display area 580 through the use of mouse, the capture image taken prior to the recording time of the representative capture image is displayed on the capture image display area 600 of the selected capture image bag 582, whereby the observer can observe the capture images (CI) sequentially taken prior to the recording time of the representative capture image grouped into the capture image bag 582, as shown in FIG. 23B.

If the observer clicks (which corresponds to the first selection, C) on at least any one of the second button areas 620 in the plurality of capture image bags 582 displayed on the sub-display area 580 through the use of mouse, the capture image taken after the recording time of the representative capture image is displayed on the capture image display area 600 of the selected capture image bag 582, whereby the observer can observe the capture images (CI) sequentially taken after the recording time of the representative capture image grouped into the capture image bag 582. At this time, the capture image selected by the observer is displayed on the main-display area 130.

Figure 23C:
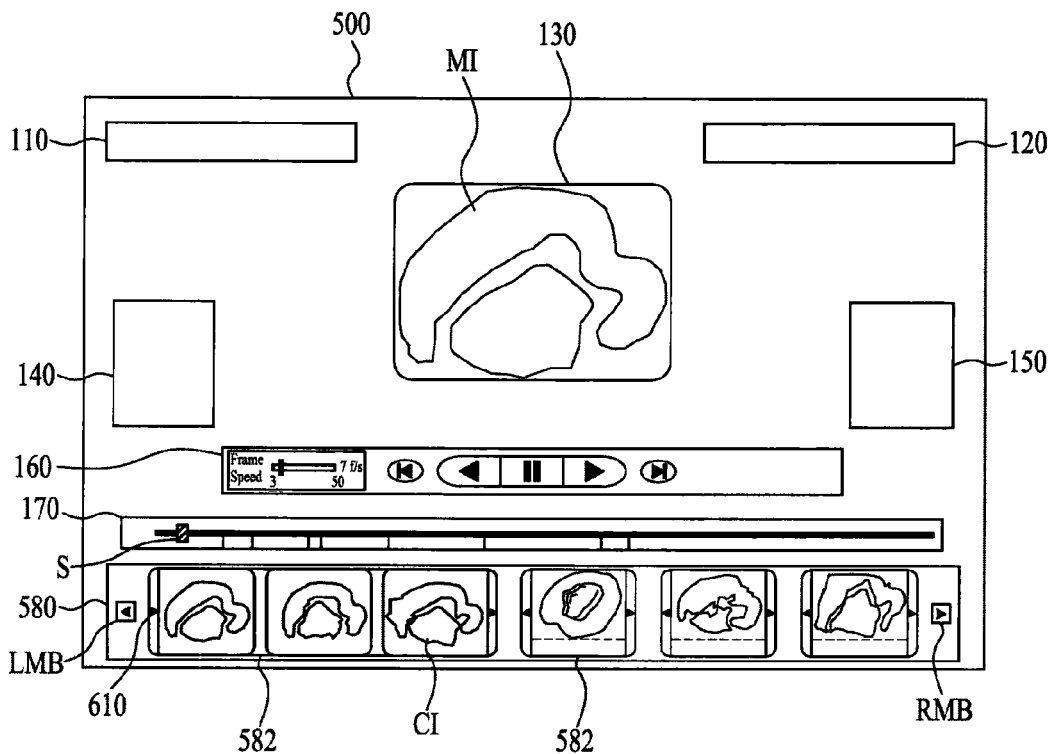

As shown in FIG. 23A, if the observer double clicks (which will be referred to as 'second selection', DC) on at least any one of the first button areas 610 in the plurality of capture image bags 582 displayed on the sub-display area 580 through the use of mouse, the capture image display area 600 of the selected capture image bag 582 is enlarged, and the capture images taken prior to the recording time of the representative capture image are displayed on the enlarged capture image display area 600 of the selected capture image bag 582, whereby the observer can observe the capture images (CI) sequentially taken prior to the recording time of the representative capture image grouped into the capture image bag 582, as shown in FIG. 23C.

If the observer double clicks (which corresponds to the second selection, DC) on at least any one of the second button areas 620 in the plurality of capture image bags 582 displayed on the sub-display area 580 through the use of mouse, the capture image display area 600 of the selected capture image bag 582 is enlarged, and the capture images taken after the recording time of the representative capture image are displayed on the enlarged capture image display area 600 of the selected capture image bag 582, whereby the observer can observe the capture images (CI) sequentially taken after the recording time of the representative capture image grouped into the capture image bag 582. At this time, the capture image selected by the observer is displayed on the main-display area 130. Also, a button direction displayed on the first button area 610 of the enlarged capture image bag 582 is changed from (◄) to (►).

If the observer double clicks (DC) on the predetermined capture image (CI) displayed on the enlarged capture image bag 582 of the sub-display area 580 through the use of mouse, or if the observer clicks or double clicks on the first button area 610, the enlarged capture image bag 582 is reduced to display on the sub-display area 580, as shown in FIG. 23A.

Referring once again to FIG. 17, it is checked whether or not the diagnosis of the in-vivo image (MI) is completed by the observer in step S1760.

If the diagnosis is completed in step S1760, it is determined that the diagnosis of the in-vivo image (MI) is completed by the observer.

If the diagnosis is not completed in step S1760, the aforementioned steps S1710 to S1750 are repetitively performed until completing the diagnosis.

The aforementioned method of displaying the capsule-endoscope image according to the embodiments of the present invention can be embodied as a program type performed by various computers including CPU, RAM, and ROM, etc., wherein the program may be stored in a computer readable storage medium, for example, hard disk, CD-ROM, DVD, ROM, RAM, or flash memory.

Accordingly, the method of displaying the capsule-endoscope image according to the present invention and the record media of storing program for carrying out the method have the following advantages.

As the capture image selected by the observer is provided together with the time bar for informing the observer of the entire time information of the capsule-endoscope image, the diagnosis efficiency can be improved.

Also, the capture image is shifted while being linked with the movement of the time slider (S), the capture image corresponding to the observer's interest is provided to the observer, thereby improving the diagnosis efficiency.

Since the time slider is linked with the movement of the capture image, the time information corresponding to the capture image shifted by the movement of the time slider is provided to the observer, thereby improving the diagnosis efficiency.

The enlarged sub-display area enables to display more capture images thereon, whereby the diagnosis efficiency can be improved.

According as the observer is provided with the text information corresponding to the diagnosis result of the capture image or the sound information about the capture image, the observer can reduce the time period consumed in writing the report and examining the diagnosis.

The observer is provided with the capture image selected by the observer or the capture image bag formed by grouping the plurality of capture images every time period, whereby the diagnosis efficiency can be improved owing to provision of the simplified capture image.

It will be apparent to those skilled in the art that various modifications and variations can be made in the present invention without departing from the spirit or scope of the inventions. Thus, it is intended that the present invention covers the modifications and variations of this invention provided they come within the scope of the appended claims and their equivalents.

What is claimed is:

1. A method of displaying a capsule-endoscope image comprising:
    generating image stream data transmitted from a swallowable capsule endoscope inserted into a body, and generating a time bar corresponding to the generated capsule-endoscope image;
    displaying the generated capsule-endoscope image on a main-display area of a first page of a diagnosis screen;
    displaying the time bar on a time bar display area of the first page of the diagnosis screen, the time bar having a time slider which indicates a position corresponding to information about time and distance of a current capsule-endoscope image displayed on the main-display area;
    displaying at least one capture image on a sub-display area of the first page of the diagnosis screen when the capsule-endoscope image displayed on the main-display area is captured;
    shifting the capture image on the sub-display area in such a way that the capture image is linked with a movement of the time slider positioned on the time bar, or moving the time slider on the time bar in such a way that the time slider is linked with a movement of the capture image; and
    when there is an observer's request for changing the size of the sub-display area: enlarging the sub-display area on the first page to display the capture images on the enlarged sub-display area on the first page, or reducing the enlarged sub-display area on the first page to the original size of the sub-display area to display the capture images on the sub-display area on the first page.

2. The method of claim 1, wherein, when the capture image is shifted in such a way that the capture image is linked with the movement of the time slider positioned on the time bar, time corresponding to a position of the moved time slider is detected, and the capture image is shifted so that other capture images having recording time being adjacent to the detected time are displayed on the sub-display area.

3. The method of claim 1, wherein, when the time slider is moved in such a way that the time slider is linked with the shift of the capture image, recording time of the reference capture image among the shifted capture images is detected, and the time slider of the time bar is moved to be corresponding to the detected recording time of the reference capsule image.

4. The method of claim 1, wherein the capture images displayed on the enlarged sub-display area are sequentially aligned according to the recording time so as to have a matrix configuration, wherein the matrix configuration may be formed in such a way that the first column is provided with the capture images having the earliest recording time among the capture images provided in each row, or in such a way that the first row is provided with the capture images having the earliest recording time among the capture images provided in each column.

5. A non-transitory recording medium storing a program for carrying out the method of claim 1.

6. A method of displaying a capsule-endoscope image comprising:

generating image stream data transmitted from a swallowable capsule endoscope inserted into a body, and generating a time bar corresponding to the generated capsule-endoscope image;

displaying the generated capsule-endoscope image on a main-display area of a first page of a diagnosis screen;

displaying the time bar on a time bar display area of the first page of the diagnosis screen, the time bar having a time slider which indicates a position corresponding to information about time and distance of a current capsule-endoscope image displayed on the main-display area;

displaying at least one capture image on a sub-display area of the first page of the diagnosis screen when the capsule-endoscope image displayed on the main-display area is captured;

shifting the capture image on the sub-display area in such a way that the capture image is linked with a movement of the time slider positioned on the time bar, or moving the time slider on the time bar in such a way that the time slider is linked with a movement of the capture image;

storing diagnosis information about the capture image;

displaying at least one icon corresponding to the capture image and including the diagnosis information on the sub-display area of the first page of the diagnosis screen; and providing the observer with the diagnosis information selected by the observer.

7. The method of claim 6, wherein the at least one icon includes a first diagnosis information icon corresponding to text information about a diagnosis result of the observer, and a second diagnosis information icon corresponding to sound information about the capture image.

8. The method of claim 7, wherein the process of providing the observer with the diagnosis information comprises:

displaying the text information on the main-display area or an additional popup window in response to the first diagnosis information icon selected by the observer; and displaying the sound information in response to the second diagnosis information icon selected by the observer.

* * * * *